(12) United States Patent
Newell

(10) Patent No.: US 6,287,773 B1
(45) Date of Patent: Sep. 11, 2001

(54) PROFILE SEARCHING IN NUCLEIC ACID SEQUENCES USING THE FAST FOURIER TRANSFORMATION

(75) Inventor: William Newell, Cambridge, MA (US)

(73) Assignee: Hoeschst-Ariad Genomics Center, Cambridge, MA (US)

( * ) Notice: Subject to any disclaimer, the term of this patent is extended or adjusted under 35 U.S.C. 154(b) by 0 days.

(21) Appl. No.: 09/314,534

(22) Filed: May 19, 1999

(51) Int. Cl.$^7$ .............................. C12Q 1/68; C12P 19/34; C12P 21/06; C07H 21/02; A61K 38/00
(52) U.S. Cl. .................................. 435/6; 435/91; 435/68; 536/23.1; 536/23.4; 530/300; 530/350
(58) Field of Search ..................... 530/300, 350; 536/23.1, 23.4; 435/91, 68, 6

(56) References Cited

U.S. PATENT DOCUMENTS

| | | | |
|---|---|---|---|
| 5,688,643 | 11/1997 | Oka et al. | 435/6 |
| 5,753,439 | 5/1998 | Smith et al. | 435/6 |
| 5,807,679 | 9/1998 | Kamb | 435/6 |

OTHER PUBLICATIONS

Benson et al., Nucleic Acids Research, 18 (21); 6305–6310 (1990).
Benson et al., Nucleic Acids Research, 18 (10); 3001–3006 (1990).
Bloomfield, P., Encyclopedia of Physical Science and Technology, 6; 651–660 (1987).
Cheever et al., 7 (2); 143–154 (1991).
Felsenstein et al., Nucleic Acids Research, 10 (1); 133–139 (1982).
Gusfield, D., Computer Science and Computational Biology, 74–77(1997).
Henikoff et al., Nucleic Acids Research, 19; 6565–6572 (1991).
Henikoff et al., Nucleic Acids Research, 27; 226–228 (1999).
Nakamura et al., Nucleic Acids Research, 27 (1); 292 (1999).
Schneider et al., Nucleic Acids Research, 18; 6097–6100 (1990).
Voss, R.F., Physical Review Letters, 68 (25); (1992).
Beston, DC, "Fourier methods for biosequence analysis", Nucleic Acids Research, Nov. 11, 1990, 18(21): pp. 6305–6310.*
Cheever, EA, et al, "Fast Fourier transform–based correlation of DNA sequences using complex plane encoding", CABIOS, Apr. 1991, 7(2): pp. 143–154.*
Yi, TM et al, "Rabbit muscle creatine kinase genomic cloning sequencing and analysis of upstream sequences important for expression in myocytes", Nucleic Acids Res, 19(11), 1991, pp 3027–3034.*
Tomandl D, et al, "Optimizing doped libraries by using genetic algorithms", J of Computer–Aided Molecular Design, Jan. 1997 11(1): 29–38.*
Nash JH, "A computer program to calculate and design oligonucleotide primers from amino acid sequences", Computer App in the Biosciences, Aug., 1993 9(4): 469–71.*
Robson KJ et al, "Molecular modelling of *malaria calmodulin* suggests that it is not a suitable target for novel antimalarials", Phil. Trans of the Royal Soc of London Series B: Biol Sci, Apr. 29, 1993, 340(1291): 39–53.*

* cited by examiner

*Primary Examiner*—John S. Brusca
*Assistant Examiner*—Stephen Siu
(74) *Attorney, Agent, or Firm*—Ivor R. Elrifi; Ingrid A. Beattie; Mintz, Levin, Cohn, Ferris, Glovsky & Popeo, PC

(57) ABSTRACT

One embodiment of the present invention provides methods for detecting known blocks of functionally aligned protein sequences in a test nucleic acid sequence, e.g., in an uncharacterized EST. The method can include the following steps. A) Reverse translate the set of protein sequences to a set of functionally aligned nucleic acid sequences using codon-usage tables and create a profile from the set of functionally aligned nucleic acid sequences. B) Construct a first indicator function for the profile. The first indicator function corresponds to adenine. The first indicator function allows the value at a given position to be continuous between 0 and 1 as a function of the percentage presence of adenine at a particular position. C) Construct a second indicator function for the test nucleic acid sequence. The second indicator function also corresponds to adenine. D) Compute the Fourier transform of each of the indicator functions. E) Complex conjugate the Fourier transform of the second indicator function. F) Multiply the Fourier transform of the first indicator function and the complex conjugated Fourier transform of the second indicator function to obtain a Fourier transform of the number of matches of adenine bases. G) Repeat steps B–F above for guanine, thymine, and cytosine. H) Sum the Fourier transforms of the number of matches for each base, respectively, to obtain the total Fourier transform. I) Compute the inverse Fourier transform of the total Fourier transform to obtain a complex series. J) Take the real part of the series to determine the total number of base matches for the variety of possible lags of the profile relative to the test sequence. The method can then detect the presence of known blocks of functionally aligned protein sequences in a test nucleic acid sequence based on the total number of base matches for the variety of possible lags.

20 Claims, 21 Drawing Sheets

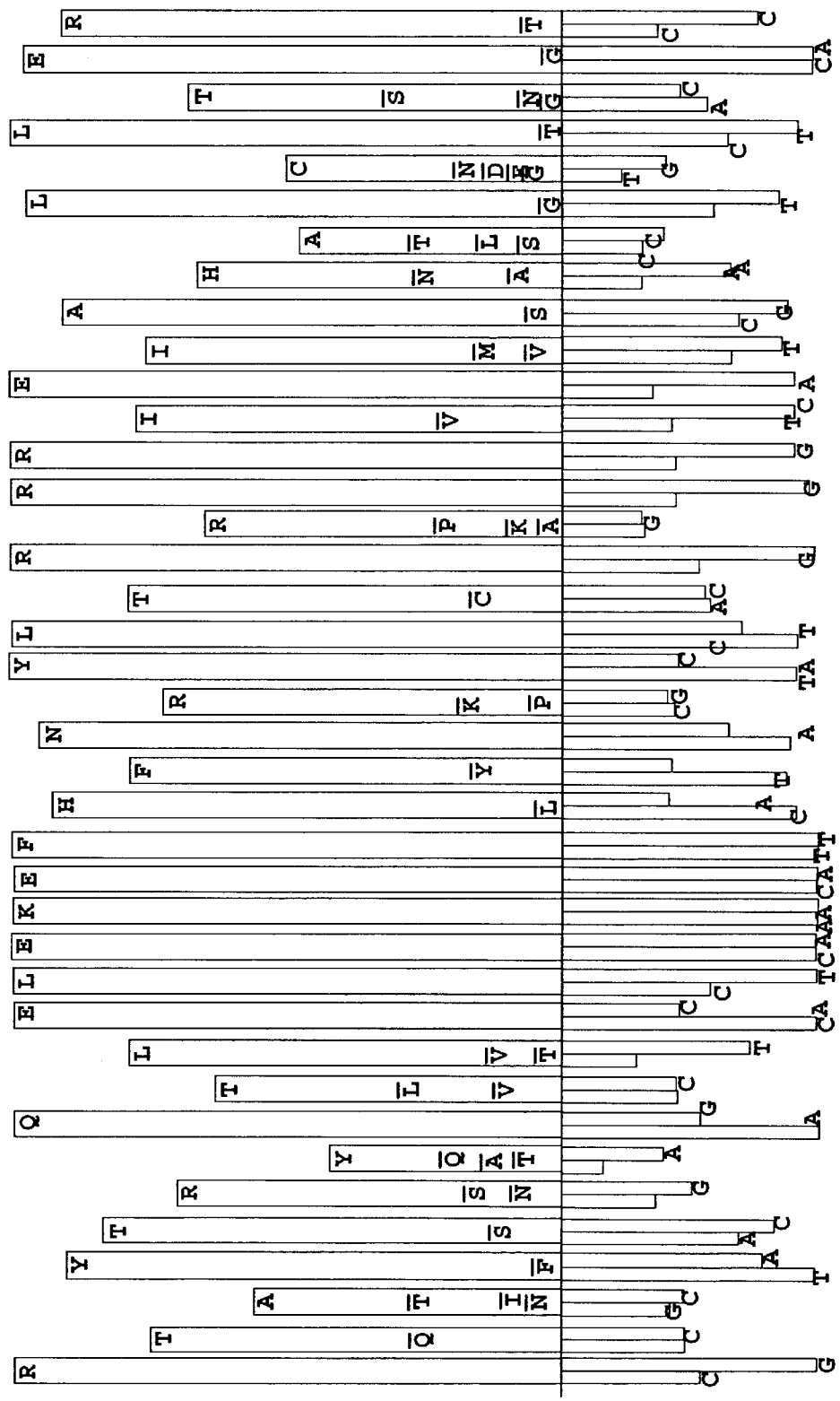

PROFILE SEARCHING IN NUCLEIC ACID SEQUENCES USING THE FAST FOURIER TRANSFORMATION

FIELD OF THE INVENTION

The present invention relates to profile searching in nucleic acid sequences, and more particularly, to detecting known blocks of functionally aligned amino acid sequences in a nucleic acid sequence, e.g., in an uncharacterized expressed sequence tag (EST), using Fast Fourier Transform (FFT) methods.

BACKGROUND OF THE INVENTION

FFT methods can facilitate the determination of the optimal global alignment of two DNA sequences. For example, Felsenstein, Sawyer, and Kochin, in "An Efficient Method for Matching Nucleic Acid Sequences," Nucleic Acids Research, Volume 10, Number 1, pp. 133–139, incorporated herein by reference, describe a method of computing the fraction of matches between two nucleic acid sequences at all possible alignments. Benson, in Fourier Methods for Biosequence Analysis, Nucleic Acids Research, Vol. 18, No. 21, p. 6305, incorporated herein by reference, and in Digital Signal Processing Methods for Biosequence Comparison, Nucleic Acid Research, Vol. 18, No. 10, p 3001, incorporated herein by reference, describes similar methods. Cheever, Overton, and Searls, in Fast Fourier transform-based correlation of DNA sequences using complex plane encoding, CABIOS, Vol. 7, No. 2, pp. 143–154, incorporated herein by reference, describe yet another variation on the use of FFT methods for the correlation of DNA sequences. These methods all use a means of coding DNA sequences as 4 binary vectors or functions (0 or 1), one vector or function for each of the 4 different bases (A, C, G, or T).

Although FFT methods can facilitate the determination of the optimal global alignment of two DNA sequences, a need remains for an efficient system for detecting known blocks of functionally aligned amino acid sequences in a nucleic acid sequence, e.g., in an uncharacterized EST.

SUMMARY OF THE INVENTION

The present invention concerns methods for detecting known blocks of functionally aligned protein sequences in a test nucleic acid sequence, e.g., in an uncharacterized EST. One embodiment of the invention provides the following steps. A) Reverse translate a set of functionally aligned protein sequences to a set of functionally aligned nucleic acid sequences using codon-usage tables and create a DNA profile from the set of functionally aligned nucleic acid sequences. B) Construct a first indicator function for the DNA profile. The first indicator function corresponds to adenine. The first indicator function allows the value at a given position to be continuous between 0 and 1 as a function of the percentage presence of adenine at a particular position. In other words if adenine occurs at a particular position in 25 out of 100 sequences, then the adenine indicator function reads 0.25 for that position in the DNA profile. C) Construct a second indicator function for the test nucleic acid sequence. The second indicator function also corresponds to adenine. D) Compute the Fourier transform of each of the indicator functions. E) Complex conjugate the Fourier transform of the second indicator function. F) Multiply the Fourier transform of the first indicator function and the complex conjugated Fourier transform of the second indicator function to obtain a Fourier transform of the number of matches of adenine bases. G) Repeat steps B–F above for guanine, thymine, and cytosine. H) Sum the Fourier transforms of the number of matches for each base, respectively, to obtain the total Fourier transform. I) Compute the inverse Fourier transform of the total Fourier transform to obtain a complex series. J) Take the real part of the series to determine the total number of base matches for the variety of possible lags of the profile relative to the test sequence. The method can then detect the presence of known blocks of functionally aligned protein sequences in a test nucleic acid sequence as a function of the total number of base matches for the variety of possible lags of the profile relative to the test sequence.

A second embodiment according to the present invention includes the following steps. A) Construct a first indicator function for a profile corresponding to known blocks of functionally aligned protein sequences. The first indicator function corresponds to adenine. The first indicator function allows the value at a given position to be continuous between 0 and 1 as a function of the percentage presence of adenine at a particular position. B) Construct a second indicator function for the test nucleic acid sequence. The second indicator function also corresponds to adenine. C) Compute the Fourier transform of each of the indicator functions. C) Complex conjugate the Fourier transform of the second indicator function. E) Multiply the Fourier transform of the first indicator function and the complex conjugated Fourier transform of the second indicator function to obtain a Fourier transform of the number of matches of adenine bases. F) Repeat steps A-E above for guanine, thymine, and cytosine. G) Sum the Fourier transforms of the number of matches for each base, respectively, to obtain the total Fourier transform. H) Compute the inverse Fourier transform of the total Fourier transform to obtain a complex series. I) Take the real part of the series to determine the total number of base matches for the variety of possible lags of the profile relative to the test sequence.

A third embodiment according to the present invention provides a system for computing the number of matches between a test nucleic acid sequence and a profile for a set of functionally aligned nucleic acid sequences. The system includes a central processing unit for executing instructions, a memory unit, and conductive interconnects connecting the central processing unit and the memory to allow portions of the system to communicate and to allow the central processing unit to execute modules in the memory unit. The memory unit includes an operating system, and several modules. A first indicator construction module constructs four first indicator functions for the profile. The indicator functions corresponding to adenine, guanine, thymine, and cytosine. The indicator functions allow the value at a given position to be continuous between 0 and 1 as a function of the percentage presence of each of the bases at a particular position. A second indicator construction module constructs four second indicator functions for the test nucleic acid sequence. The second indicator functions correspond to adenine, guanine, thymine, and cytosine. A Fourier transform module computes the Fourier transform of each of the indicator functions. A complex conjugation module complex conjugates the Fourier transforms of the four second indicator functions. A multiplication module multiplies the Fourier transforms of the first indicator functions and the conjugated Fourier transforms of the second indicator functions for each of the bases, respectively, to obtain Fourier transforms for adenine, guanine, thymine, and cytosine matches. A summation module sums the Fourier transforms of the number of matches for each base, respectively, to obtain the total Fourier transform. A computation module computes the inverse Fourier transform of the total Fourier transform to obtain a complex series. The computation module also takes the real part of the series to determine the total number of base matches for the variety of possible lags of the profile relative to the test sequence.

The number of computational steps required using an FFT method is proportional to NlogN where N is the number of bases in the longest sequence. The number of computational steps using spatial domain methods is proportional to $N^2$. Thus, if N is large enough, FFT methods are computationally more efficient than spatial domain methods for detecting known blocks of functionally aligned amino acid sequences in a nucleic acid sequence. In a preferred embodiment, the test nucleic acid sequence can be any length between an EST and a chromosome. More specifically, the test nucleic acid sequence can have a length of from approximately 10 kilobases to approximately 100 kilobases. In a preferred embodiment, the set of functionally aligned amino acid sequences can consist of from approximately 5 to approximately 30 amino acids. Consequently, the corresponding DNA profile will consist of from approximately 15 to approximately 90 bases. Correlation is a floating-point operation, and is therefore well-suited to matching a sequence against a profile, where the profile comprises probabilities of distinct residues at particular positions in an alignment.

BRIEF DESCRIPTION OF THE DRAWINGS

FIGS. 4A–4C show the same series of FIGS. as FIGS. 3A–3C for antennapedia-like protein instead of the 14-3-3 protein diagnostic block.

DETAILED DESCRIPTION OF THE INVENTION

Figure 1:
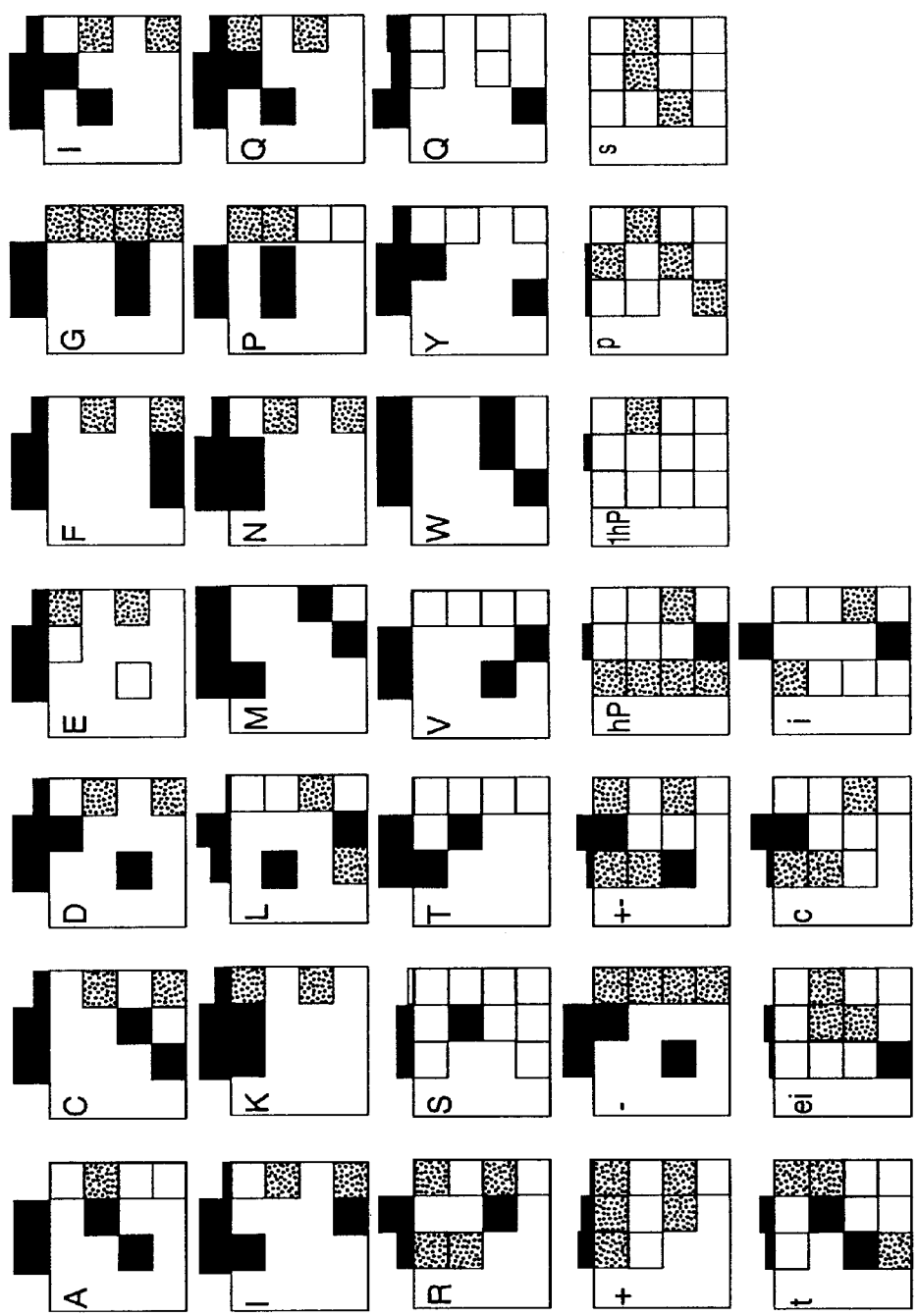
FIG. 1 shows five rows of 4×3 matrices indicating the relative frequencies of bases in the codons that make up individual amino acids (e.g., matrices in rows 1–3) and that make up groups of amino acids (e.g., matrices in rows 4 and 5).

Many protein patterns are diagnostic of protein families and/or function. These patterns are often reported as alignments of blocks of similar protein sequence. One is often interested in detecting protein sequence patterns in uncharactexized DNA sequences, rather than in uncharacterized protein sequences. A preferred embodiment of a method according to the invention searches DNA sequences for the presence of such blocks. This method reverse-translates common protein alignments (e.g. BLOCKS, Pfam) to nucleic acid profiles. The method reverse-translates the common protein alignments using recently tabulated codon frequencies. The method then performs a search for the known nucleic acid profiles by obtaining the correlation of different bases between a test nucleic acid sequence and the known nucleic acid profile. This is efficiently achieved in the frequency (Fourier) domain by use of a Fast Fourier Transform (FFT).

Reverse-translating the protein sequences into DNA sequences allows direct searching for protein patterns in DNA. This method has several advantages: (i) compared to other methods, the reverse-translation/FFT method is relatively insensitive to DNA sequencing errors, e.g. insertions and deletions, and can assist in detecting such errors; (ii) the method avoids the need for a costly 6-frame translation of DNA to protein; (iii) the anti-sense strand can be searched in an efficient manner, due to the reversal theorem of the discrete Fourier transform (DFT); (iv) the method does not require continuous exact matches, as required by BLAST-BLAST can miss significant and important matches due to insertion of a single amino acid in a protein sequence, even though the single inserted amino acid does not adversely affect function; (v) the coding of protein sequences to DNA can be generalized to code protein function signatures, e.g. "match 7 hydrophobic residues".

Consider a block or set of aligned protein sequences consisting of N (typically between 5 and 50) residues. According to one embodiment, systems and methods of the present invention construct a profile of the set of aligned protein sequences. The profile, which indicates the frequency of amino acids for each of the N residues, can take the form of a 20×N matrix, in which the 20 rows correspond to the frequencies of the 20 distinct amino acids (A to Y) that make up proteins, and the N columns correspond to the N positions of the residues in the profile. The entry $p_{ij}$ then contains the observed frequency of amino acid i at position j in the alignment. This matrix is typically sparse, since at each sequence position only a few of the possible 20 amino acids are represented. The sum of each column is 1.

Each column in the protein profile is converted to a 4×3 matrix of corresponding DNA base frequencies, in which the 4 rows correspond to the average frequencies of the 4 different bases, and the 3 columns represent positions 1 to 3 in a codon. If there is only one amino acid present at a particular position in the protein alignment, the 4×3 matrix is the base frequency matrix for that amino acid. If there are two or more amino acids present at a particular position in the protein profile, the 4×3 base composition matrix is obtained as the weighted sum of the base frequency matrices of the amino acids present, the weights being the observed frequency of the different amino acids at that position.

The 20×N amino acid frequency matrix is thereby converted to a 4×3N base frequency matrix. The number of symbols is reduced from 20 to 4, but the number of sequence positions increases from 1 to 3. The overall reduction in space requirements is 40%.

FIG. 1 shows five rows of 4×3 matrices indicating the relative frequencies of bases in the codons that make up individual amino acids (e.g., matrices in rows 1–3) and that make up groups of amino acids (e.g., matrices in rows 4 and 5). The data were derived from numbers of different codons observed in the public sequence database GenBank, as reported by Nakamura, Y, Gojobori, T and Ikemura, T. in Codon usage tabulated from the international DNA sequence databases, Nucleic Acids Res. 27, 292–292 (1999), incorporated herein by reference. For each amino acid, the number of codons was recorded. The frequency of use of different codons for the same amino acid was then calculated and represented as an average base frequency. The 4×3 matrix thus includes four rows corresponding to the four bases A, C, G, and T, and three columns corresponding to the positions in the codon. For example, tryptophan (W) is represented by only one codon (TGG), which is reflected in the plot as base frequencies $p_{T1}=1$, $P_{G2}=1$, $P_{G3}=1$. Glycine (G) is coded by 4 different codons, all of which have the same two bases in the first two positions (GG). The bases in the third, "wobble", position are used with almost equal frequency. The frequencies in each column sum to 1.

The histogram directly above each 4×3 matrix is the degree of conservation, or non-randomness of base frequencies at each of the three positions in the codon. The maximum value of the conservation is 1, which is achieved when only one of the four bases is observed at a particular position, and its minimum value is 0 when all 4 bases occur with equal frequency 0.25.

The 4$^{th}$ and 5$^{th}$ rows of the five rows of FIG. 1, represent base frequencies for collections of amino acids having similar properties. The groups are defined below, in the order in which they occur in FIG. 1.

| Symbol | meaning | amino acids in the group |
|---|---|---|
| + | positively-charged | R,H,K |
| − | negatively-charged | D,E |
| +− | charged | R,H,K,D,E |
| hPh | hydrophobic | A,I,L,M,F,P,W,V |
| !hPh | hydrophilic | R,N,D,C,Q,E,G,H,K,S,T,Y |
| p | polar | N,C,Q,G,S,T,Y |
| s | small | P,V,C,A,G,T,S,N,D |
| t | tiny | A,G,S |
| ei | unbiased to location | A,C,G,P,S,T,W,Y |
| e | external | R,N,D,Q,E,H,K |
| I | internal | I,L,M,F,V |

Using these symbols, it is possible to define less specific patterns which have biological meaning. For example, signal sequences, diagnostic or secreted or cell-surface proteins, can be described by the more general pattern: "1–5 positive residues, followed by 7–15 hydrophobic residues, followed by 3–7 polar, uncharged residues."

Figure 2:
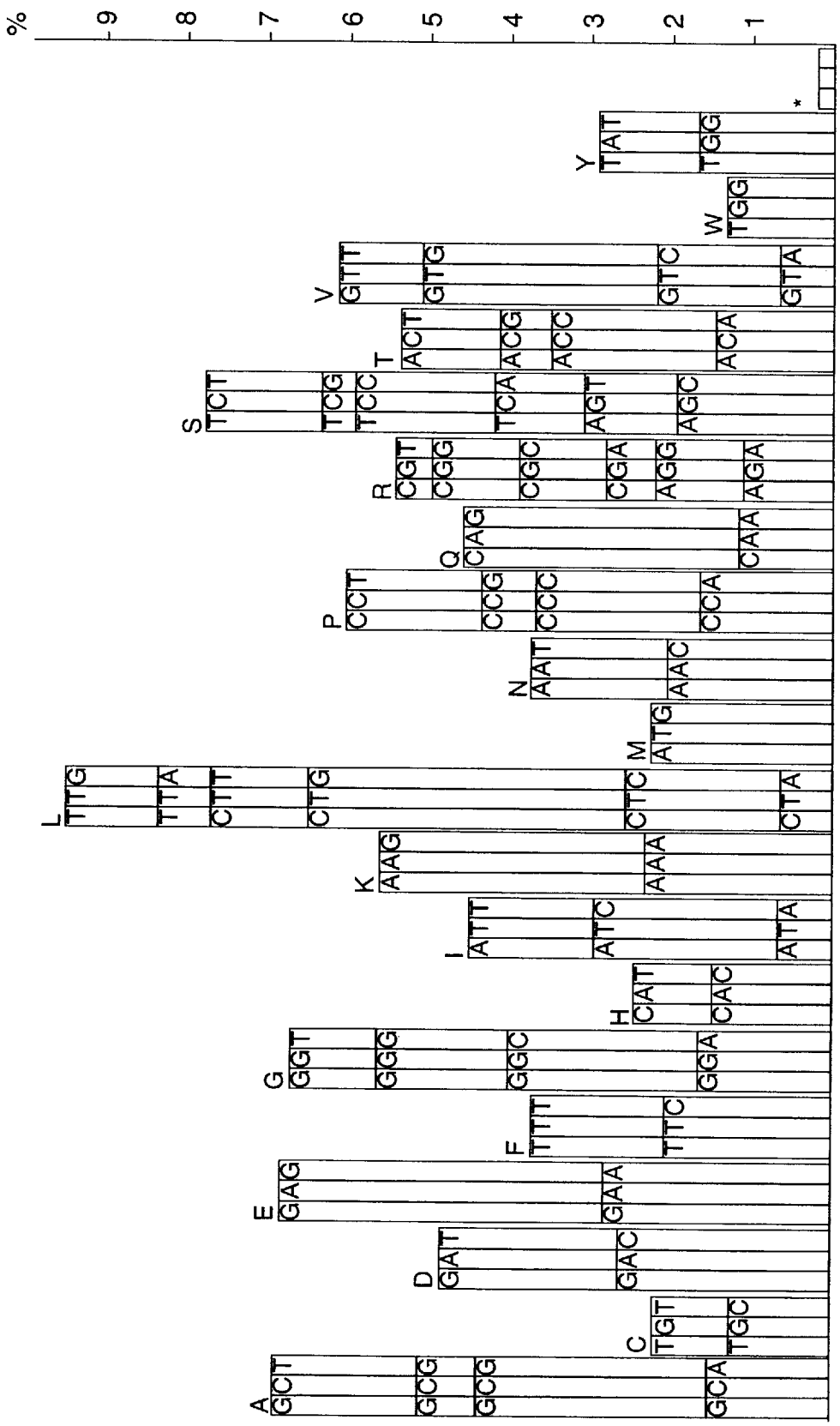
FIG. 2 is a histogram showing the relative frequencies of the codons that make up each of the twenty amino acids and that make up the stop codons (*)—the relative frequencies of the codons are used to construct the 4×3 matrices of FIG. 1.

FIG. 2 is a histogram showing the relative frequencies of the codons that make up each of the 20 amino acids, and that make up the stop codons (*). The relative frequencies of the codons are used to construct the 4×3 matrices of FIG. 1. Leucine (L) is the most abundant amino acid (9.6%), followed by Serine (S) (7.9%). The stop codons are the least frequently used codons (0.2%). The relative frequencies of the amino acids are also used to give composite base frequencies for the amino acids groups in rows 4 and 5 of FIG. 1.

Figure 3A:
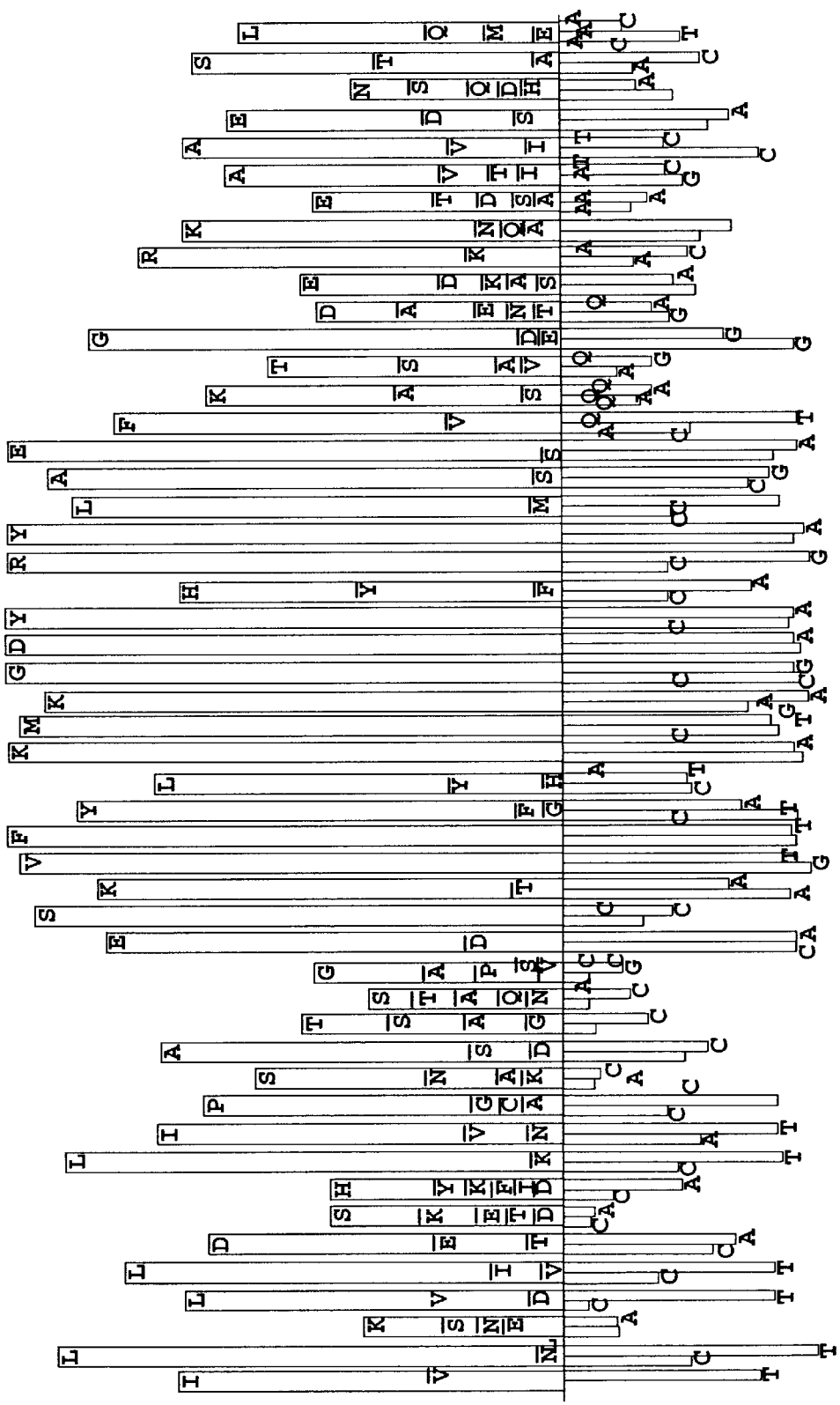
FIG. 3A shows profiles of a 14-3-3 protein diagnostic block where the profile above the X axis is a protein profile and the profile below the X axis is a DNA profile.

FIG. 3A is a graph showing the profiles of a 14-3-3 protein diagnostic block. The graph is split horizontally in two parts. The profile above the X axis is a protein profile. The profile below the X axis is a DNA profile obtained by reverse-translating the protein profile. These profiles show an example of a protein functional block, from the BLOCKS database. See Henikoff, S and Henikoff, J G, in Automated assembly of protein blocks for database searching, Nucleic Acids Res. 19, 6565–6572 (1991), incorporated herein by reference, and Henikoff, J G, Henikoff, S and Pietrovski, S, in New features of the Blocks Database servers, Nucleic Acids Res. 27, 226–228 (1999), incorporated herein by reference.

The height of the bar at each sequence position in the protein profile is proportional to the degree of conservation of the position. Conservation is related to statistical entropy. This type of display was first shown by Schneider T D and Stephens R M, in Sequence logos: a new way to display consensus sequences, Nucleic Acids Res. 18, 6097–100 (1990), incorporated herein by reference. This display was termed a sequence "logo". The maximum degree of conservation is $\log_2(20)=4.32$ bits, since there are 20 different amino acids. The minimum degree of conservation is 0, when all amino acids are used with equal frequency. Completely conserved positions are observed in the central region of the block. Within each bar, the relative abundance of the different amino acids at that position is indicated by divisions in the bar.

For the DNA profile, the relative frequencies of the bases at the three different codon positions for each of the protein sequence positions were calculated as described above. The degree of conservation of the bases in the resulting reverse-translated profile is then calculated for each of the 3N DNA sequence positions. Again, the bars are scaled according to the conservation.

Figure 3B:
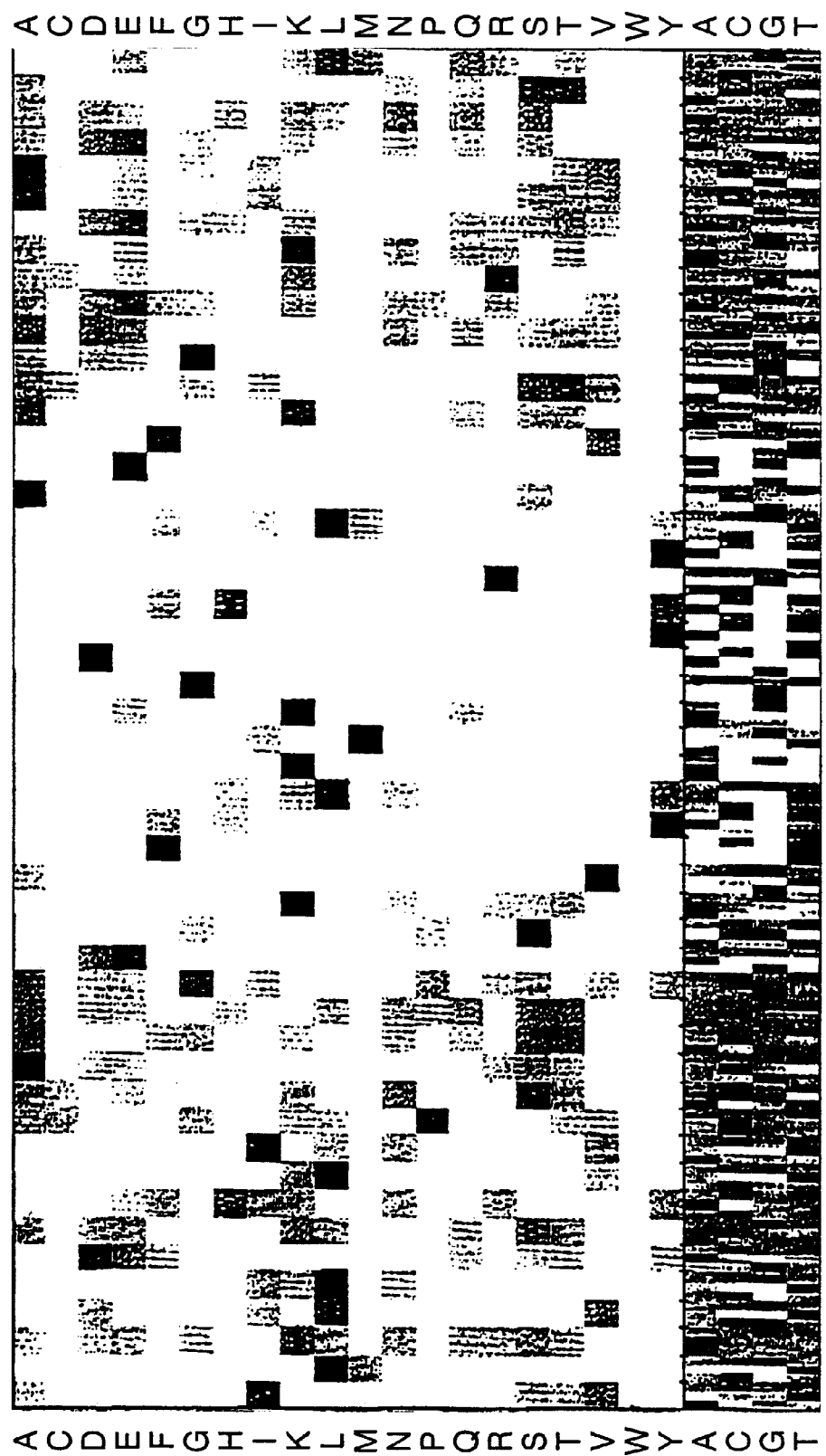
FIG. 3B shows the profiles of FIG. 3A in matrix form with the individual matrix elements shown in grayscale (1=black, 0=white).

FIG. 3B shows the frequencies of the amino acids observed at the different sequence positions as a grayscale (1=black, 0=white). The corresponding DNA base frequencies are shown in the lower part of the figure.

Figure 3C:
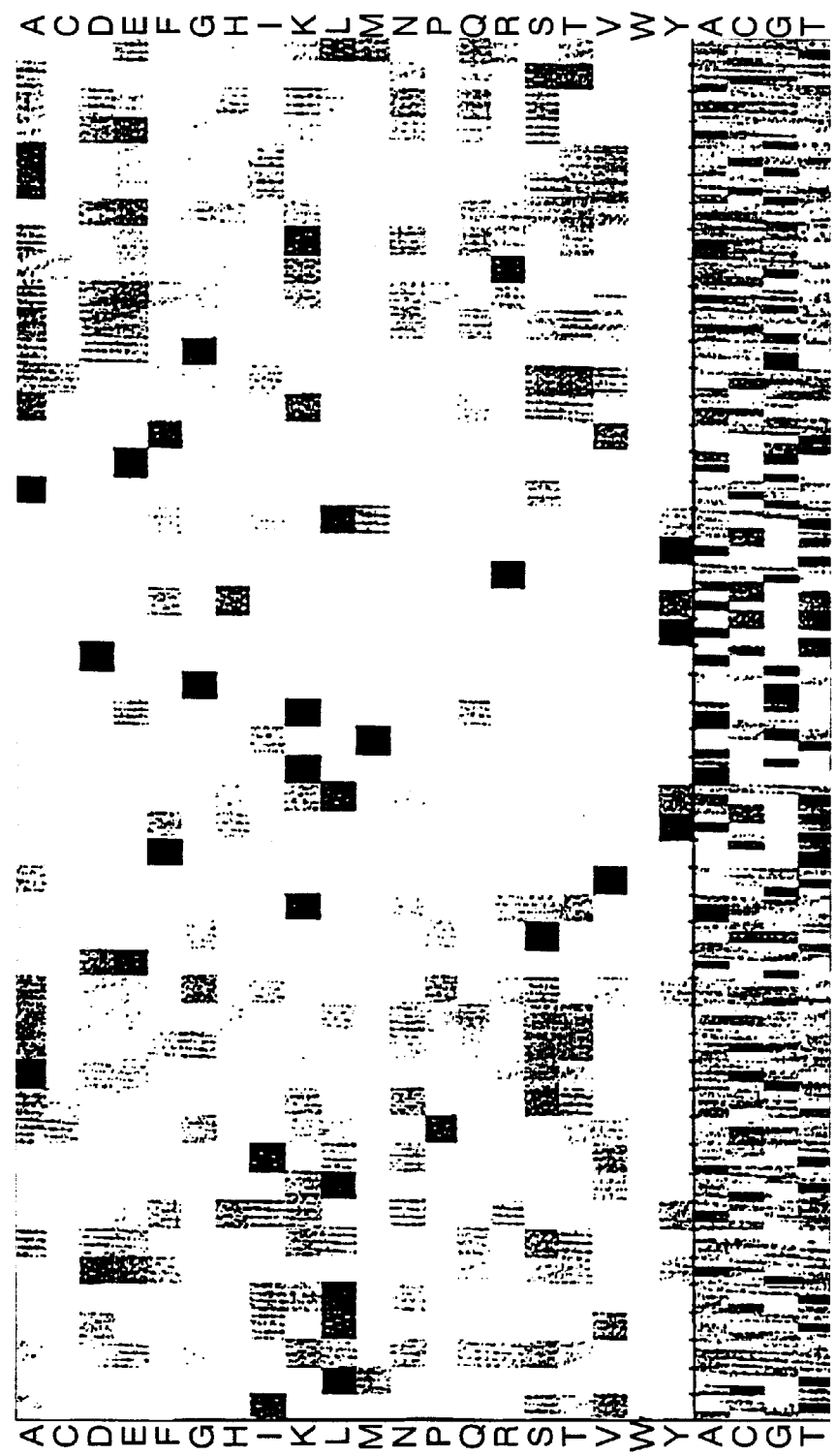
FIG. 3C shows the frequencies in FIG. 3B weighted according to the degree of sequence conservation at each position in the alignment.

FIG. 3C shows the frequencies in FIG. 3b are weighted according to the degree of sequence conservation at each position in the alignment. Weighting of the profile emphasizes residues at the right end and in the middle of the profile. Compared to the use of an unweighted profile, the use of a weighted profile for a correlation provides a more accurate indication of the presence of a particular motif in a DNA sequence. Weighting the profile provides a more accurate indication of the presence of a particular motif because weighting the profile incorporates more information about the motif into the profile. For example, a situation where a residue is completely conserved, and where the bases corresponding to the residue match in the query or test sequence, provides 2 bits of information that the motif is present. At the other extreme, if all 4 bases are observed at a particular position in the reverse translated DNA profile, this position gives no additional information about the positive occurrence of the motif in the query sequence, since any base will give an equally good match. Positions with intermediate levels of conservation are given correspondingly intermediate weights.

Subsequent to determining the DNA profile of the protein block of interest, the coding of the resulting DNA profile to numerical vectors is accomplished by a modification of the binary vector methods for single sequences described earlier. According to those methods a single sequence is broken into four vectors, one for each base. A particular base's vector takes on a value of 0 or 1 for a specified position depending on whether the particular base is present at that position in the sequence. The present method again makes 4 vectors, but their values are continuous between 0 and 1 and correspond to the weighted or unweighted observed frequency of the 4 bases in the reverse-translated profiles. Thus, the present method extends the FFT technique to allow the "value" of a base at a given position to be continuous between 0 and 1. One embodiment of this extension of the FFT technique allows comparison of a DNA sequence against a DNA profile representing a set of aligned DNA sequences. The set of aligned DNA sequences, derived from a set of aligned protein sequences, might differ at individual positions. For example, one position might have a T in 75% of the sequences, and an A in 25% of the sequences. The "value" of this position is therefore 0.75 in the T vector, and 0.25 in the A vector.

Thus, one embodiment of a method according to the present invention begins by reading the profile and the test sequence and constructing a series of indicators, i.e., vectors, one for each of the four bases. Each of these is an array containing a value ranging from zero to one based on the percentage presence of the base at a given position. For example, the sequence AACGTGGC has the four indicator sequences:

Sequence: AATGCGGT
Indicator for A: 11000000
Indicator for T: 00100001
Indicator for G: 00010110
Indicator for C: 00001000

According to one embodiment, when a base at a certain position is unknown, the method sets all four indicator values to 0.25, and when it is only known that a base at a particular position is (for example) a purine, this embodiment of the invention sets two of the indicator values to 0.5 and the other two to zero. The j-th entry in the indicator function for A can be denoted as $P_j^{(A)}$, and the indicator functions for the other three bases can be similarly denoted. The corresponding indicator function for the profile can be denoted by $Q_j^{(A)}$.

The number of matches of A's when the second sequence is displaced by k from the first is then given by:

$$R_k^{(A)} = \sum_{j=1}^{n} P_j^{(A)} Q_j^{(A)} \tag{1}$$

The overall number of matches at a shift of k is given by $$R_k = R_k^{(A)} + R_k^{(C)} + R_k^{(G)} + R_k^{(T)} \tag{2}$$

Note that the convention we have adopted for missing information implies that when an unknown base lies opposite a known one, we count one-fourth of a match.

The foundation of this method is the relation between convolutions and Fourier transforms: if P and Q are sequences whose discrete Fourier transforms are U and V, then the sequence R giving the number of matches has the Fourier transforms W, where $$W_j = U_j V_j^* \tag{3}$$

where the star indicates the complex conjugate (changing the sign of the imaginary part of the complex number $V_j$).

The FFT method of the invention computes the total Fourier transform in a number of operations proportional to N ln N. The FFT method computes the Fourier transforms of the indicator functions of the test sequence and of the indicator functions for the profile representing the set of functionally aligned nucleic acid sequences. This computation results in eight Fourier transforms. Each of the Fourier transforms is a sequence of complex numbers. The complex conjugates of the sequences $V_j^{(A)}, \ldots, V_j^{(T)}$ are then taken (which can be done in n operations each). One embodiment of a method according to the invention can then use equation (3) to compute the Fourier transforms $W_j^{(T)}$ which are the transforms of the numbers of matches of A's, C's, G's and T's at all possible shifts.

Since the Fourier transform is a linear transformation, the transform of a sum is the sum of transforms. This means that if we are interested only in the overall number of matches, without regard to which of the four nucleotides is matching, we can sum the four W's to get:

$$W_j = W_j^{(A)} + W_j^{(C)} + W_j^{(G)} + W_j^{(T)}. \tag{4}$$

We now take the inverse Fourier transform of the sequence $W_j$. The real parts of the resulting sequence of complex numbers will be the numbers of matches at shifts 0, 1, ..., N. The complex parts of the result will all be zero. We have thus obtained the result we wanted with 9 Fourier transforms, each of which requires on the order of N ln N operations. Since databases of functional protein alignments are updated only periodically, complete alignment databases are stored as their Fourier transforms, avoiding the need to recalculate for each search.

Previous methods for matching sequences to a sequence "profile" use dynamic programming techniques which scale as $O(N^2)$. This method scales as $O(N \ln N)$. For two sequences of length 10 kb, the time saving is of the order of 1000.

The information content in protein profiles and reverse-translated DNA profiles are compared, and used to formulate an unbiased scoring scheme which is independent of the size of the database being searched.

One utility of this approach is to rapidly and sensitively detect matches to known protein sequences which are characteristic of well-defined function, where otherwise there would be no means of detecting such functions, in completely uncharacterized DNA. This is of timely application, in the era of large-scale EST sequencing. Many new EST sequences have been found not to match any known DNA sequences in the public or proprietary sequence databases. It is expected that this method will enable at least partial characterization of such sequences, by a more sensitive search against smaller and more specific protein sequence motifs. The computer memory requirement for the method is O(N), making it suitable for use on smaller computers.

Examples of protein motifs that embodiments of the invention can search for include transmembrane regions defined by stretches of hydrophobic residues, antigenic regions defined by stretches of hydrophilic regions, EF-hand which occurs in calcium binding proteins, helix-turn-helix motif which occurs in the DNA binding motif, zinc finger which occurs in the DNA binding motif, and glycosylation motif, a post translational protein modification. Examples of DNA profiles that embodiments of the invention can search for include promoters and enhancers.

The FFT methods of the present invention advantageously are computationally efficient relative to correlations in the spatial domain. Such computational efficiency reduces computer memory and processing requirements. Furthermore, such computational efficiency allows for the processing of larger collections of profiles and longer sequences than would be possible using spatial domain methods.

Searching in DNA sequences, rather than protein sequences avoids costly 6-frame translation, detects the correct reading frame automatically, and detects indels. In addition, the methods of the present invention provide for matching of a test sequence and a profile sequence with one of the sequences in reverse orientation simply by removing the step of complex conjugation.

Figure 4B:
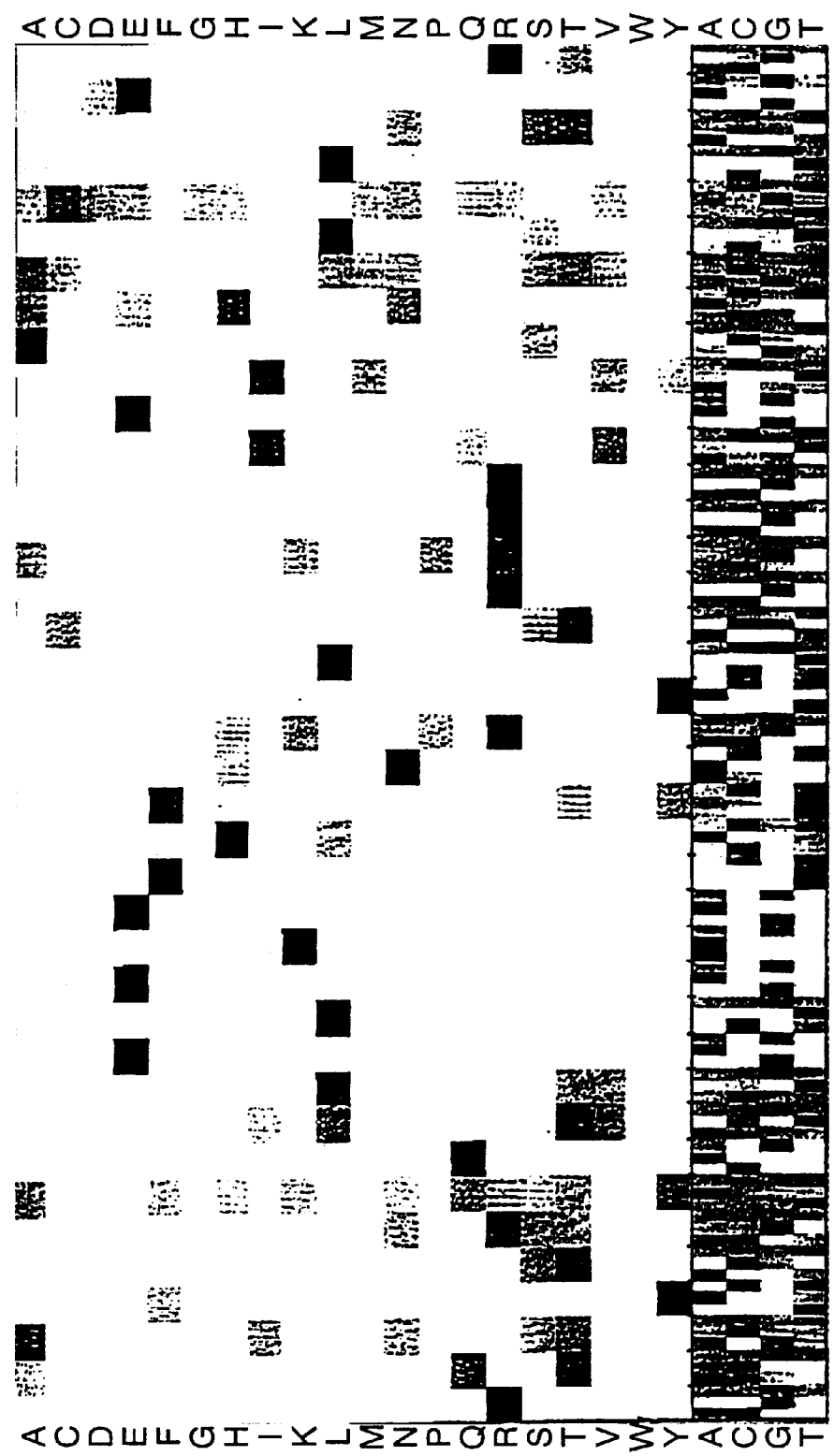
Figure 4C:
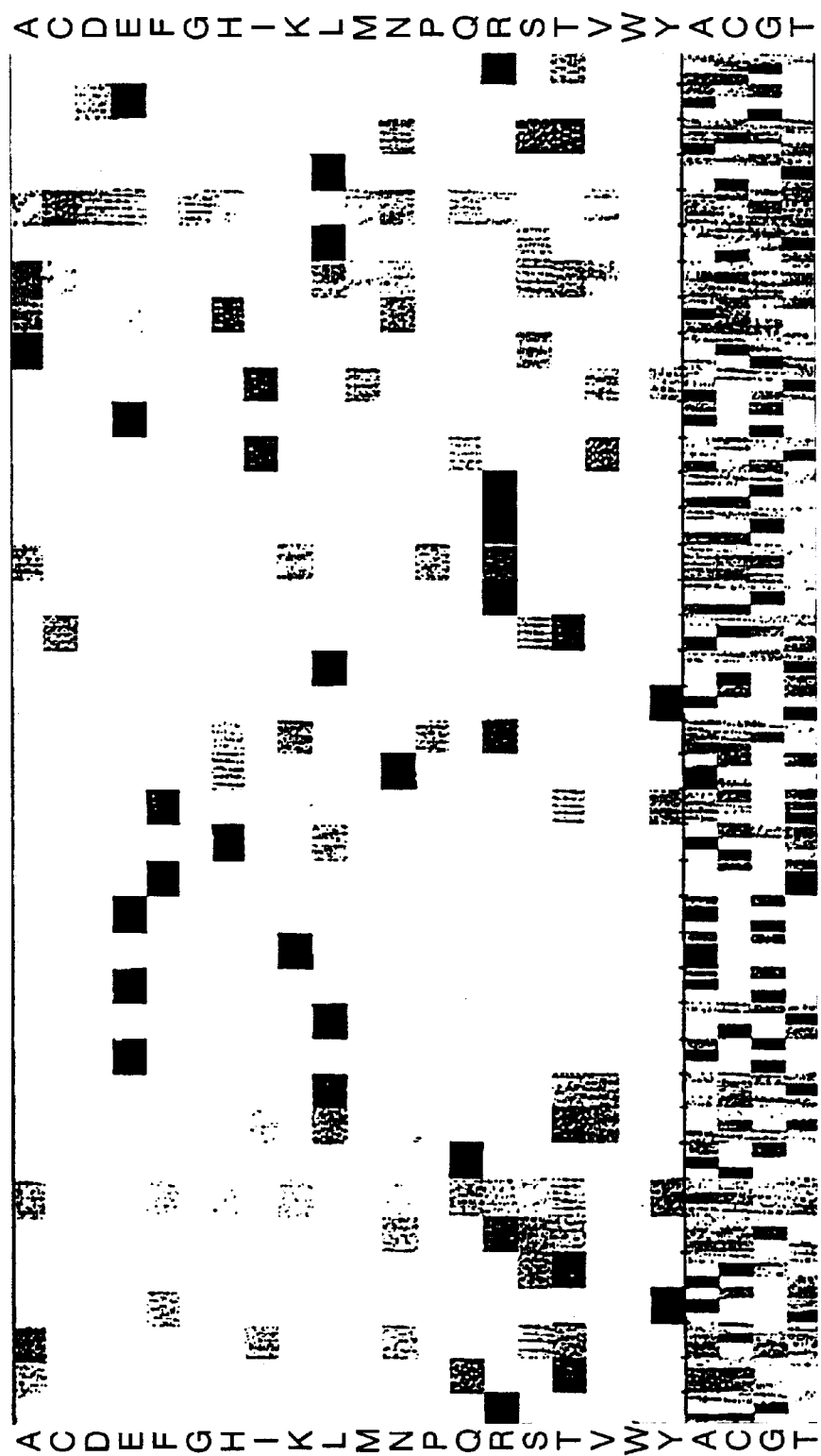
Figure 5A:
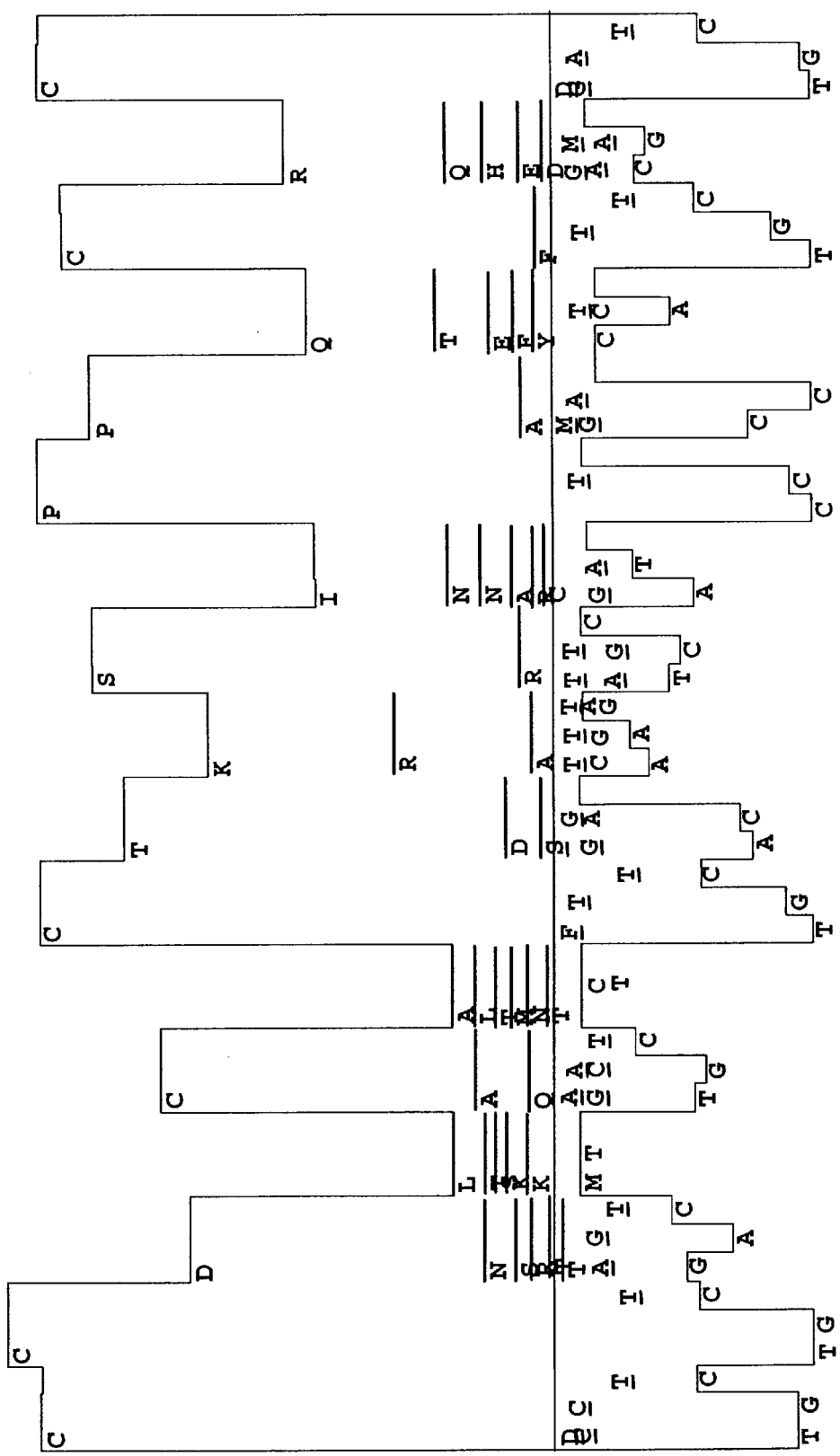
FIGS. 5A–5C show the same series of FIGS. as FIGS. 3A–3C for the Bowman-Birk serine protinase inhibitors family instead of the 14-3-3 protein diagnostic block.
Figure 5B:
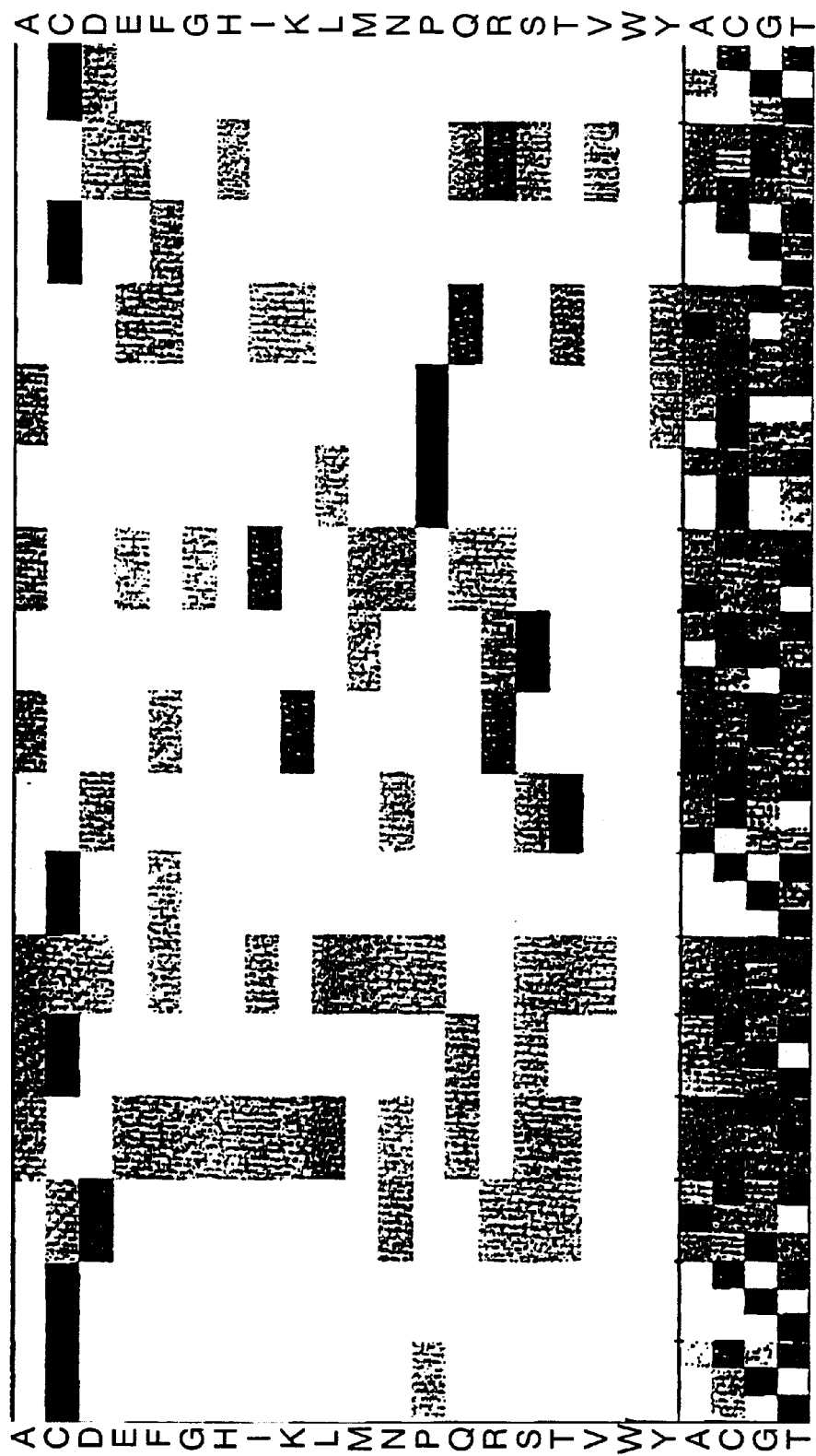
Figure 5C:
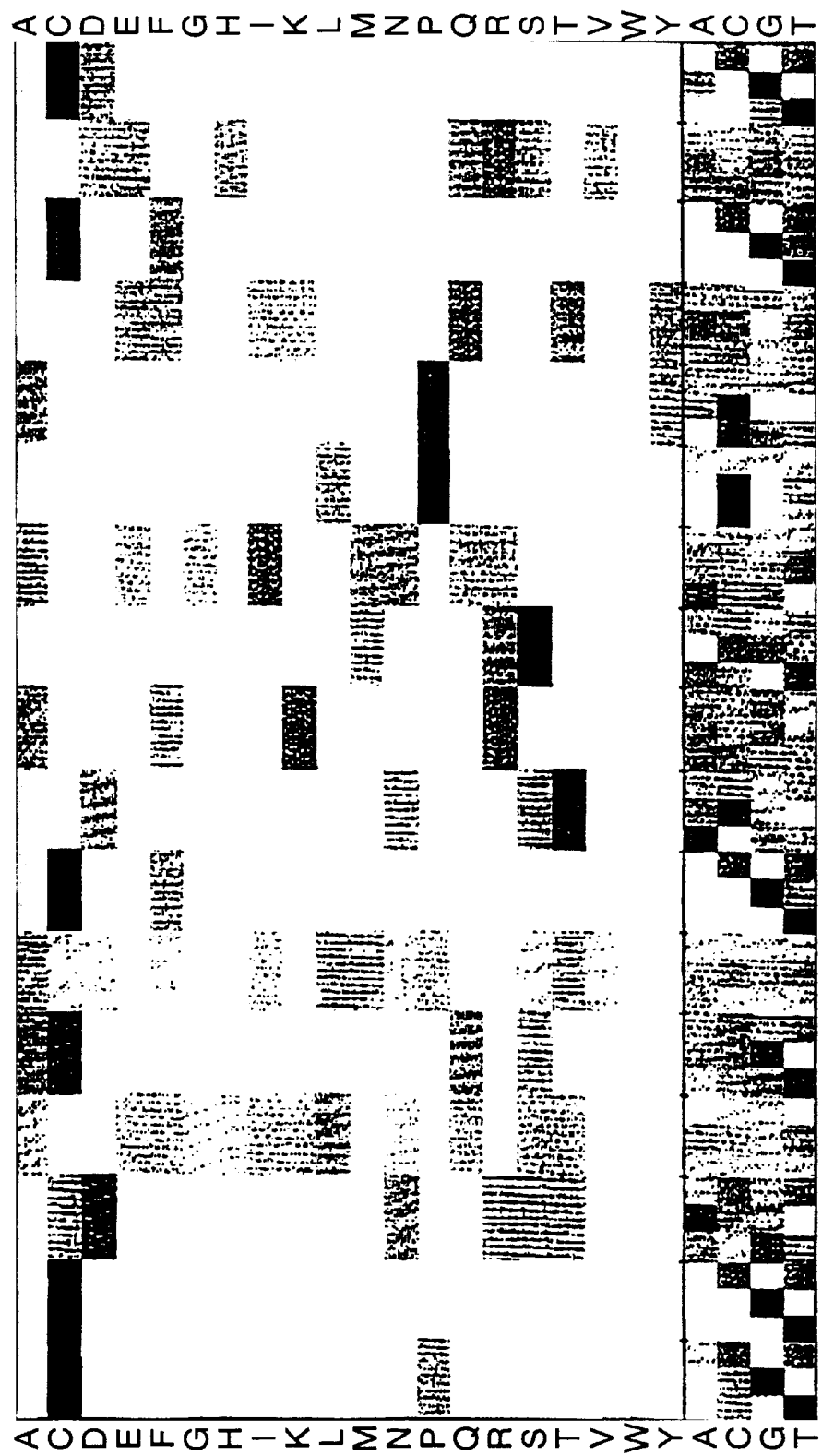
Figure 6:
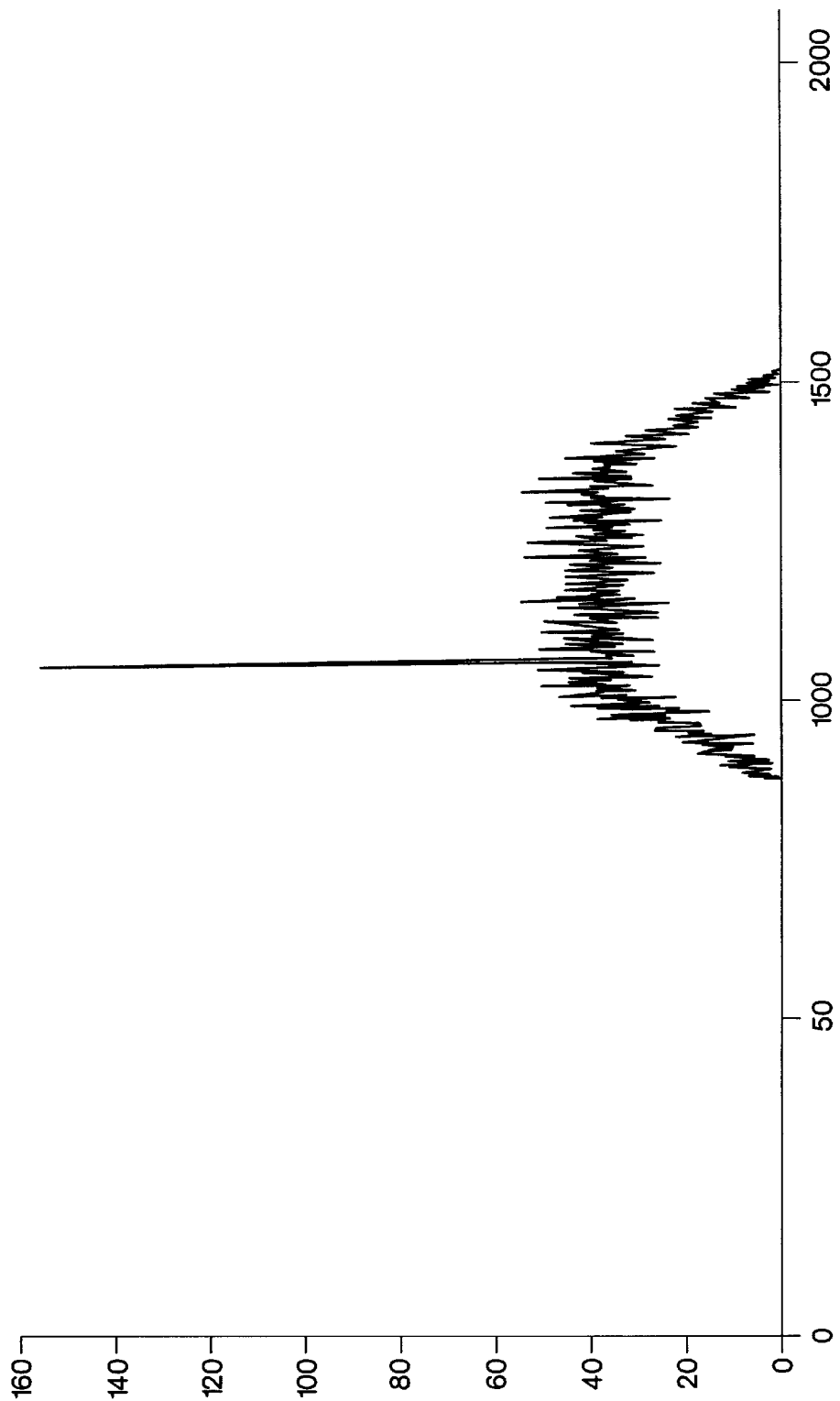
FIG. 6 is a graph illustrating the match of a subsequence to a larger randomly generated sequence which entirely contains the subsequence—the X axis is the lag between the subsequence and the larger sequence, and the Y axis is the correlation (degree of similarity) between the subsequence and the larger sequence.

FIGS. 4A–4C show the same series of FIGS. as FIGS. 3A–3C for antennapedia-like protein instead of the 14-3-3 protein diagnostic block. FIGS. 5A–5C show the same series of FIGS. as FIGS. 3A–3C for the Bowman-Birk serine protinase inhibitors family instead of the 14-3-3 protein diagnostic block;

FIG. 6 is a graph illustrating the match of a subsequence to a larger randomly generated sequence which entirely contains the subsequence. The X axis is the lag, from −1024 to +1023. A negative lag means that the start of the first (longer) sequence lies to the left of the start of the shorter sequence. A positive lag means that the start of the longer sequence lies to the right of the start of the shorter sequence. A lag of zero means that the start positions of the two sequences coincide.

The Y axis is the correlation (degree of similarity) between the two sequences at all possible lags −1024 to +1023. The parent sequence was constructed randomly using a uniform base frequency (probability of each base= 0.25). It is 500 bp long. The subsequence starts at base 45 in the parent sequence, and is 155 base pairs long. The spike in the correlation occurs at the lag at which the two sequences match best. It is clearly visible above the noise, and its value, 155, confirms the randomly-chosen length of the subsequence. The start of the subsequence at base 45 in the longer sequence is also shown as the distance from the left side of the flat part of the random correlation. The value of the random correlation is approximately 40, which is to be expected for the length of the subsequence. This follows from the probability of matches occurring by random to be $p=\Sigma_{i=1,4}p_{ii}$. For equally distributed bases, this probability is 0.25. The average correlation in the flat part of the correlation plot, when the subsequence is entirely contained within the larger sequence, is centered around 155*0.25=39.

Figure 7:
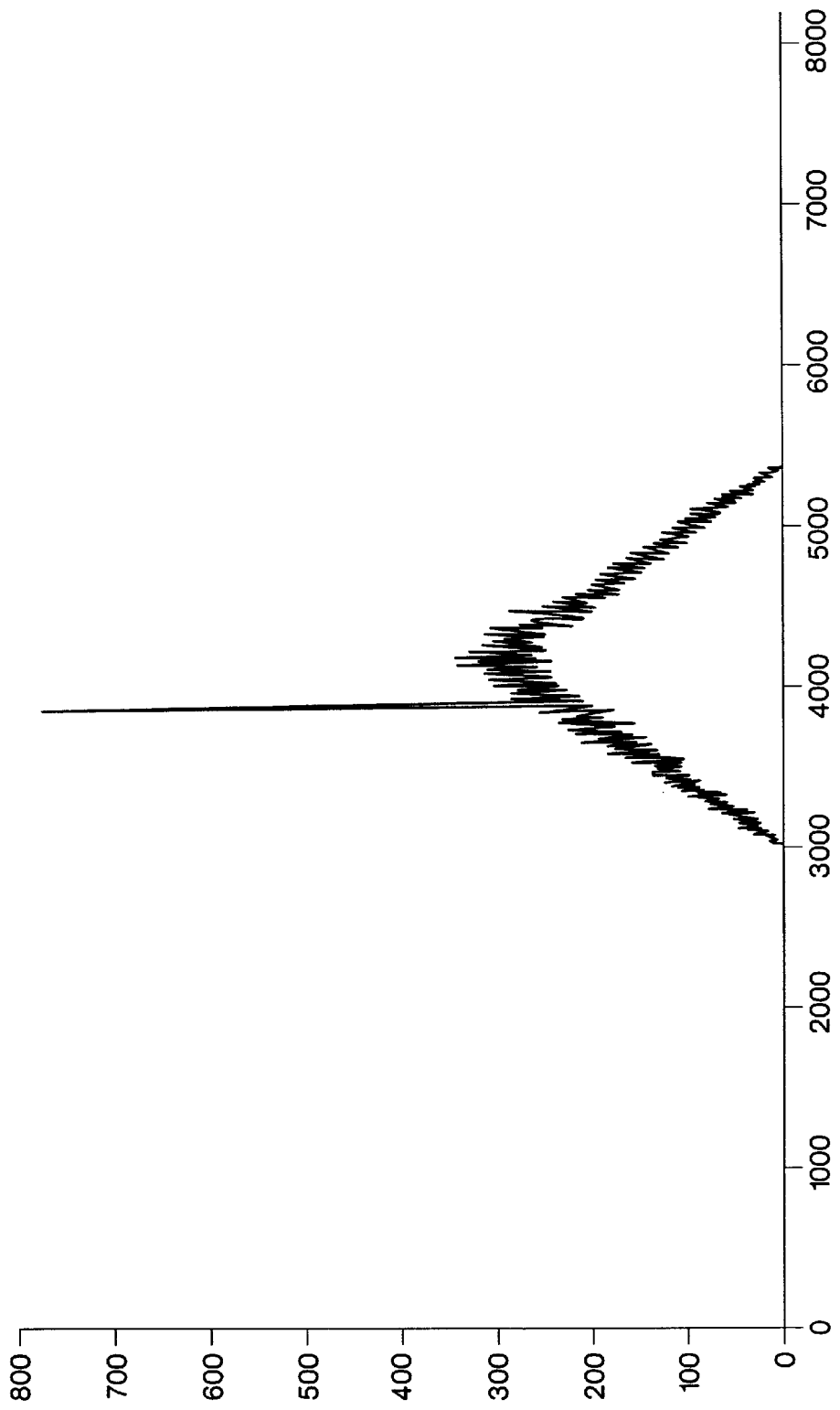
FIG. 7 is a graph similar to FIG. 6 illustrating the match of GenBank sequence M28207 (Homo sapiens (clone pMF17) MHC class 1 HLA-Cw7 MRNA, 3' end) to a DNA profile of all HLA-C sequences constructed from the data in hladb (ftp://ftp.ebi.ac.uk/pub/databases/imgt/mhc/hla/).

FIG. 7 is a graph similar to FIG. 6 illustrating the match of GenBank sequence M28207 (Homo sapiens (clone pMF17) MHC class 1 HLA-Cw7 MRNA, 3' end) to a DNA profile of all HLA-C sequences constructed from the data in hladb (ftp://ftp.ebi.ac.uk/pub/databases/imgt/mhc/hla/). The length of the complete HLA-sequence is 1101 bp. The presence of this profile in sequence M28207 is clearly demonstrated by the large peak in the correlation spectrum, and defines the position of the correct alignment (lag) unambiguously.

Figure 8:
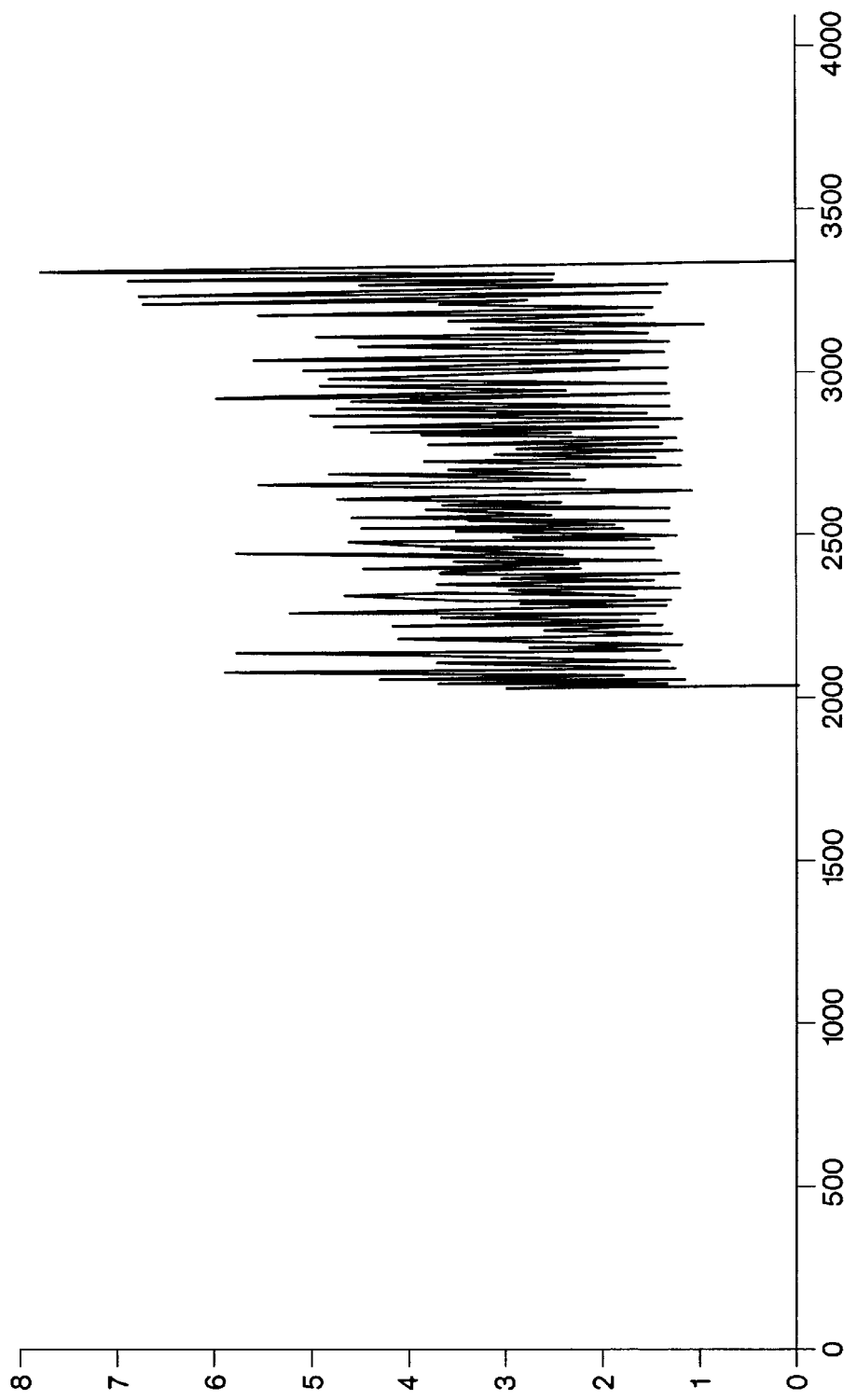
FIG. 8 is a graph similar to FIG. 6 illustrating the match of a profile for a polyA site in the sequence M28207.

FIG. 8 is a graph similar to FIG. 6 illustrating the match of a profile for a polyA site in the sequence M28207. The profile for a polyA site is shown with those of other DNA regulatory elements in FIG. 10. Although the polyA signal is very weak, the method still correctly identifies it at the correct position where the maximum correlation occurs.

Figure 9:
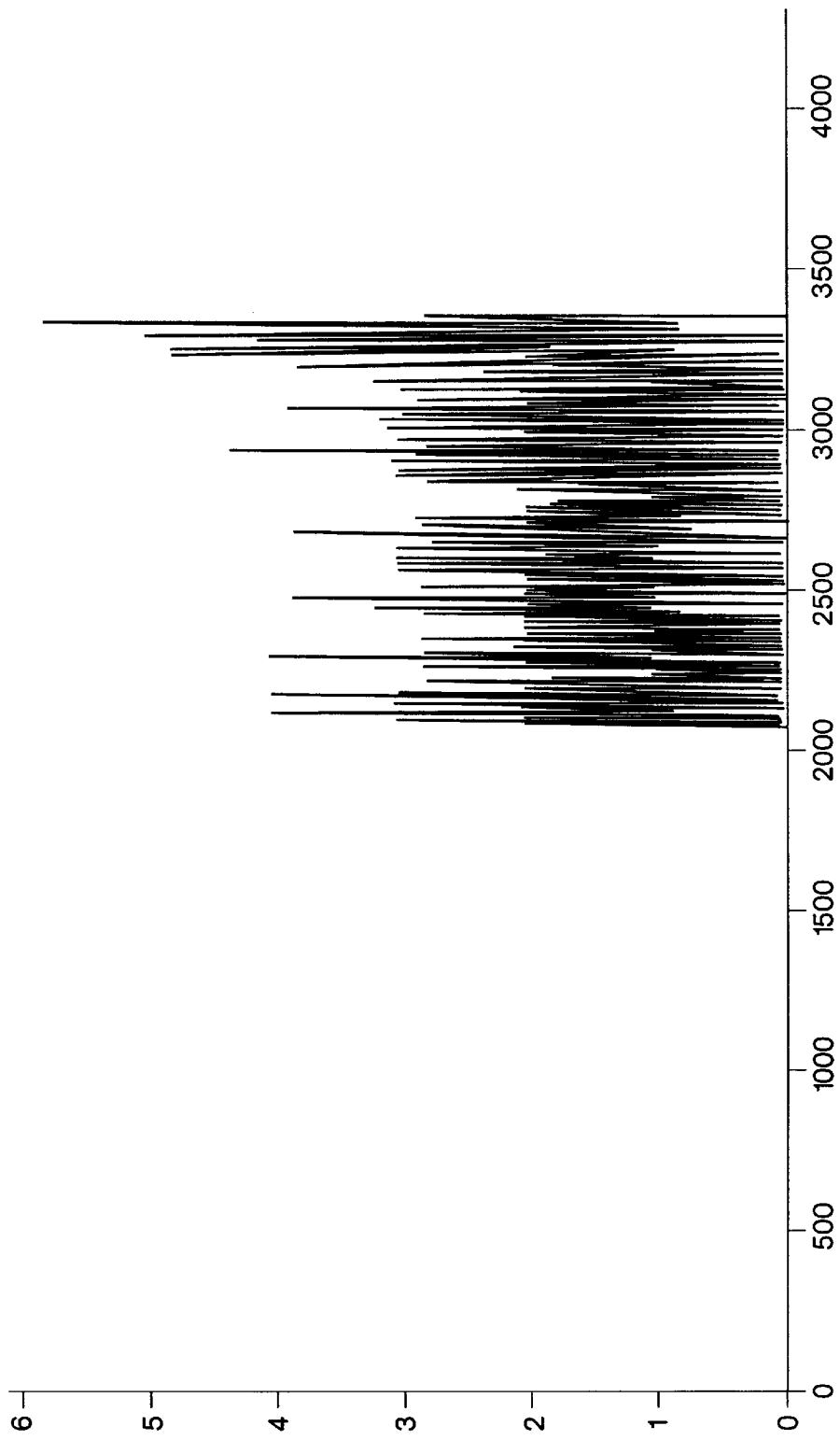
FIG. 9 is a graph similar to FIG. 8 illustrating the match of a profile for a polyA site in the sequence M28207 where the profile for the polyA site has been weighted by the sequence conservation of the motif.

FIG. 9 is a graph similar to FIG. 8 illustrating the match of a profile for a polyA site in the sequence M28207 where the profile for the polyA site has been weighted by the sequence conservation of the motif The discrimination of the polyA site in M28207 is slightly improved by matching it against the profile of PolyA, weighted by the sequence conservation of the motif.

Figure 10:
FIG. 10 shows the profiles of some common DNA regulatory elements.

FIG. 10 shows the profiles of some common DNA regulatory elements. Row 101 shows the unweighted profiles for the elements. Row 102 shows the weighted profiles for the elements. Row 103 shows the sequence conservation for the elements.

Figure 11:
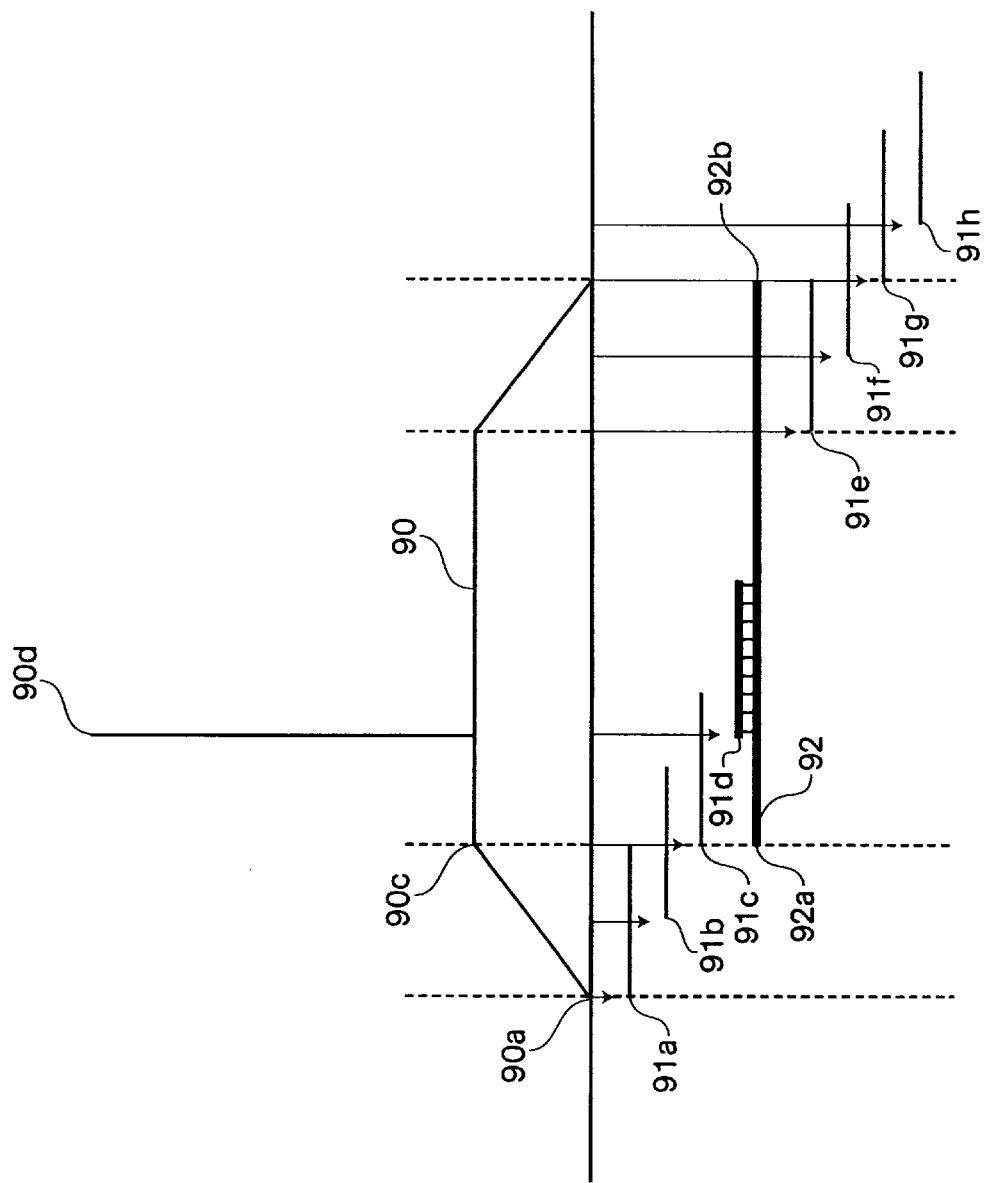
FIG. 11 is a schematic showing the association of a correlation plot with a variety of lags between a subsequence and a larger sequence.

FIG. 11 is a schematic showing the association of a correlation plot with a variety of lags between a profile and a test sequence. FIG. 11 aids in the interpretation of correlation plots such as FIGS. 6–9. Correlation plots show correlation 90 (the Y axis) as a function of lag (the X axis). The X-axis is the lag between profile 91 and test sequence 92. In FIG. 11, the correlation 90 is plotted as profile 91 (shorter sequence) slides across test sequence 92 (longer sequence). In this example, the profile 91 is completely contained within the test sequence 92. The peak 90d in the correlation occurs where profile 91 completely matches a portion of test sequence 92. Its value is the length of profile sequence 91.

Figure 12A:
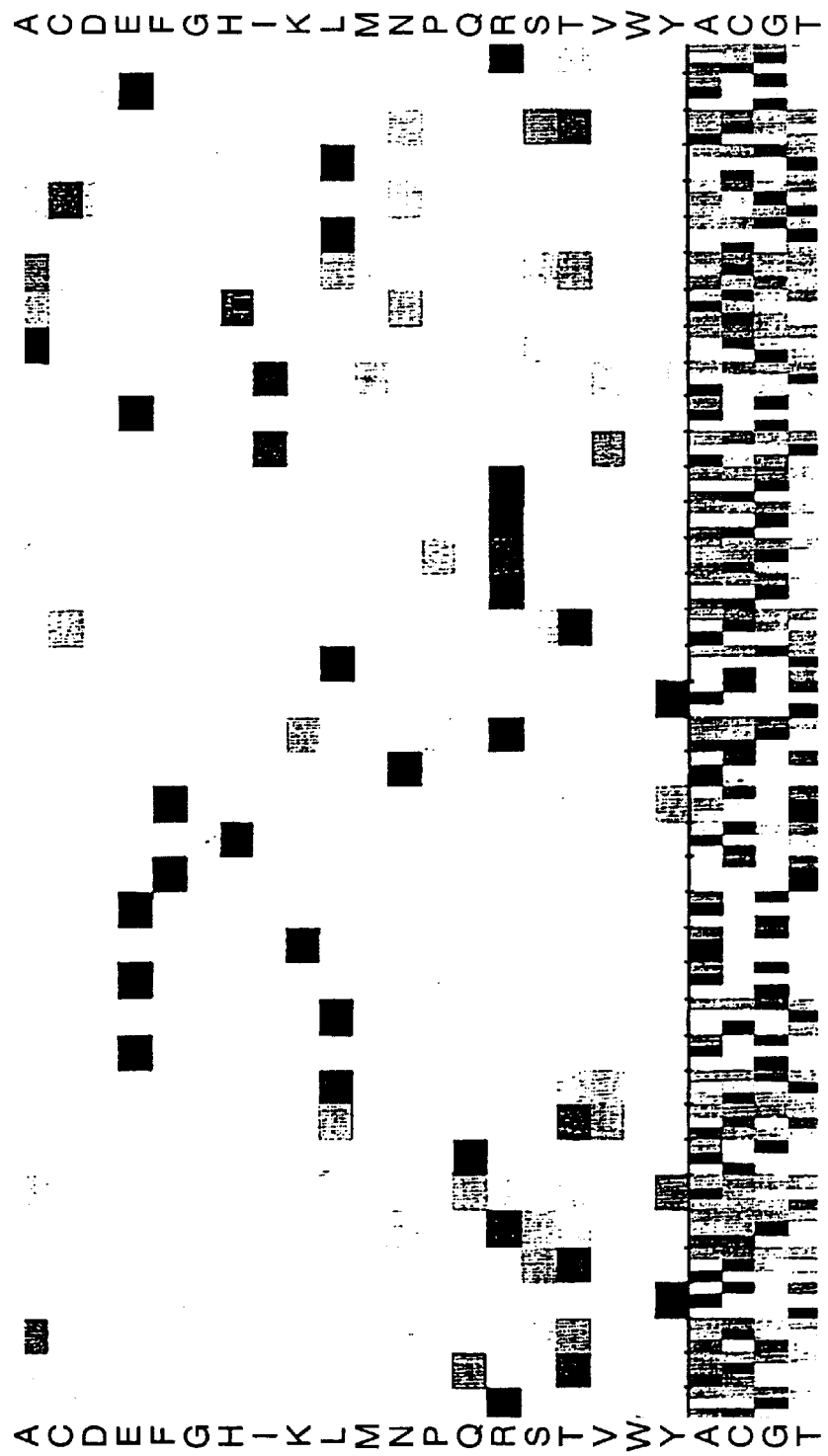
FIGS. 12A and 12B, similar to FIGS. 3B and 3C, are unweighted and weighted profiles, respectively, for a block diagnostic of the antennapedia-type protein family.
Figure 12B:
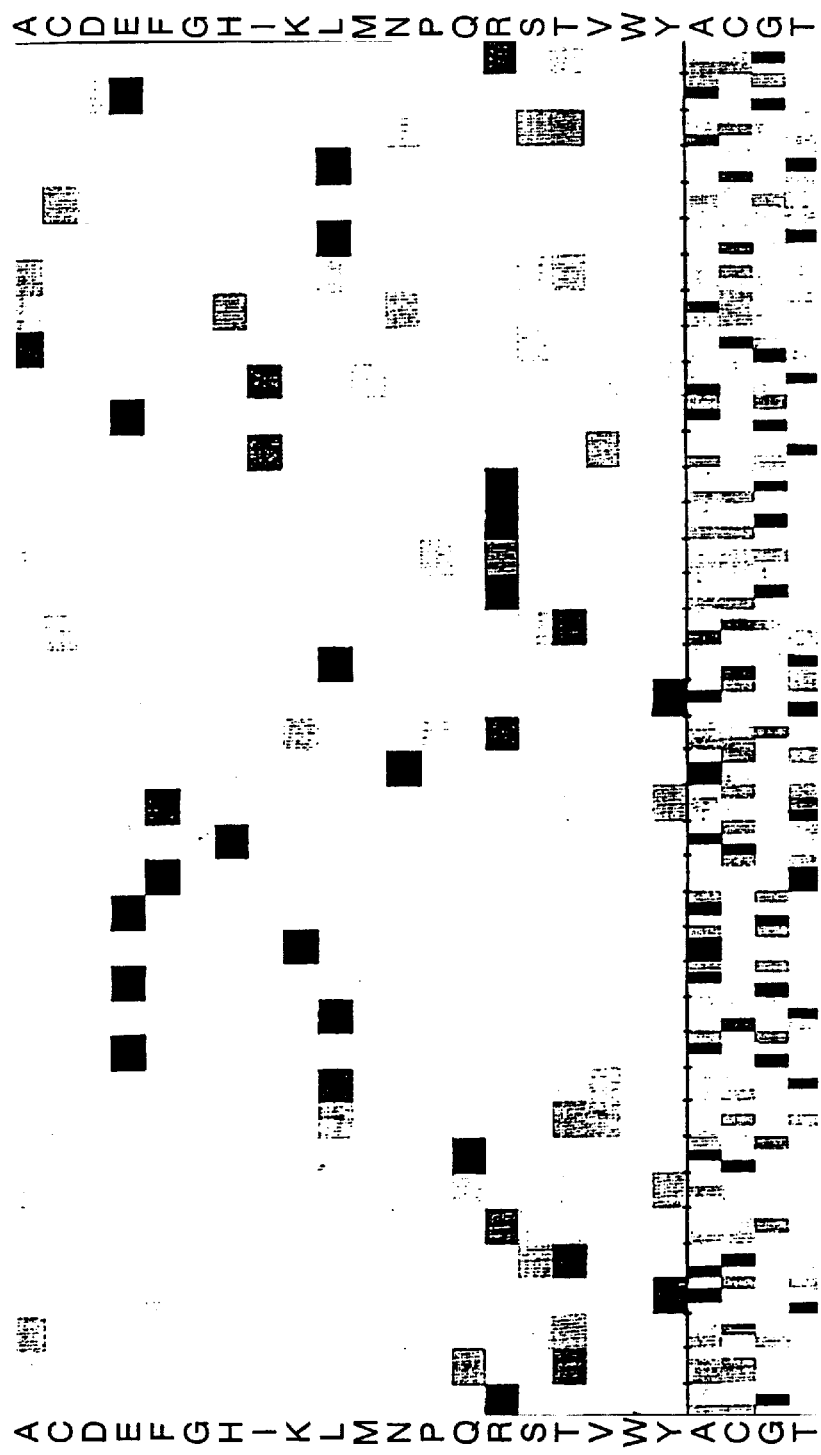
Figure 13A:
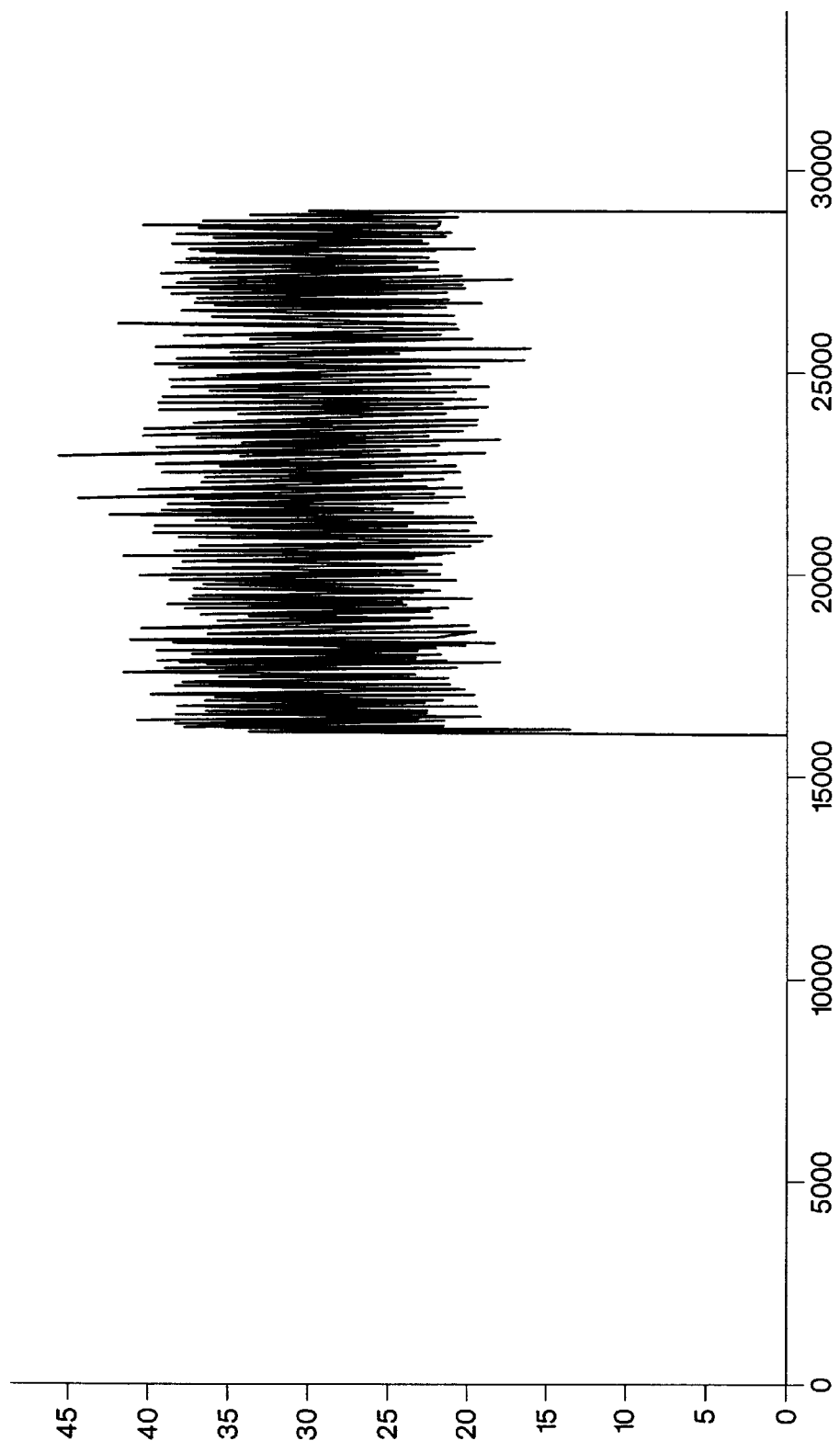
FIG. 13A is a graph similar to FIG. 6 illustrating the match of a profile for the antennapedia block in the genomic clone derived from P1 close DS00189 from *Drosophila melangaster* (fruitfly).

FIGS. 12A and 12B, similar to FIGS. 3B and 3C, are unweighted and weighted profiles, respectively, for a block diagnostic of the antennapedia-type protein family. FIG. 13A is a graph, similar to FIG. 6, illustrating the match of a profile for the antennapedia block in the genomic clone derived from P1 clone DS00189 from *Drosophila melangaster* (fruitfly) (GenBank accession AC001654). This clone is reported to contain the antennapedia complex containing homeotic genes, but its exact location is not reported in the primary reference (http://www.ncbi.nlm.nih.gov/htbin-post/Entrez/query?iud=2342707&form=6&db=n&Dopt=g). FIG. 13A is a correlation of AC001654 with the unweighted antennapedia protein profile. The main peak is observed at x-coordinate approx. 23000. The magnitude of the background correlation is approx. 30, and the maximum correlation approx. 45. The ratio of the main peak to the background is ~1.5.

Figure 13B:
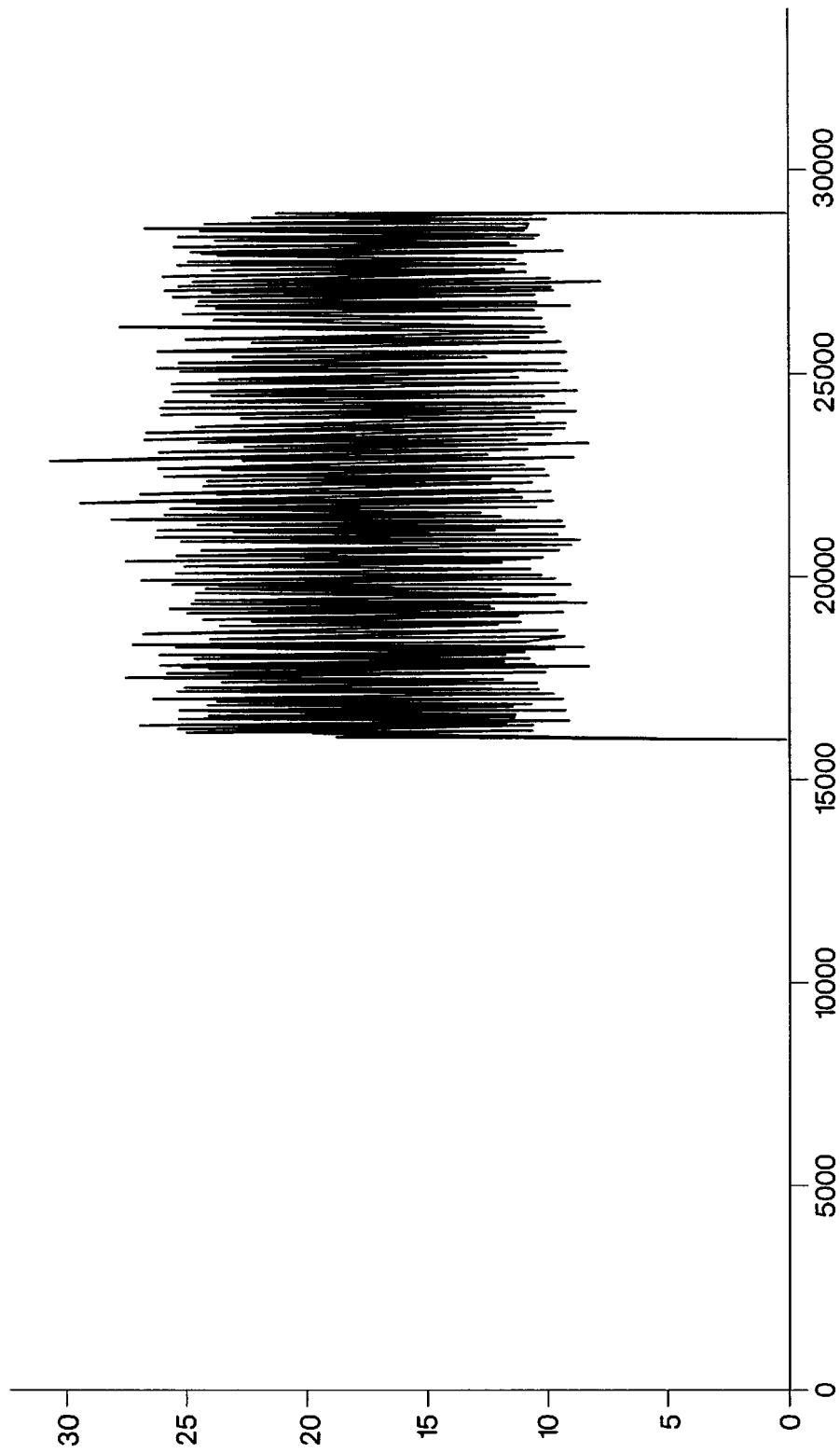
FIG. 13B is a graph similar to FIG. 13A illustrating the match of a profile for the antennapedia block in the genomic clone derived from P1 close DS00189 from *Drosophila melangaster* (fruitfly) where the profile for the antennapedia site has been weighted by the sequence conservation of the motif

FIG. 13B is a graph, similar to FIG. 13A, illustrating the match of a profile for the antennapedia block in the genomic clone derived from P1 close DS00189 from *Drosophila melangaster* (fruitfly) where the profile for the antennapedia site has been weighted by the sequence conservation of the motif. FIG. 13B is a correlation of AC001654 with the weighted antennapedia profile. The background correlation is approx. 17, and the value of the main peak is about 31. The ratio is ~1.8. Use of the weighted profile therefore increases the discrimination of the method.

Those skilled in the art will appreciate that the invention may be embodied in other specific forms without departing form the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A method of computing the number of matches between a test nucleic acid sequence and a profile for a set of functionally aligned nucleic acid sequences comprising the steps of
    A) constructing a first indicator function for the profile, said indicator function corresponding to a first base, said indicator function allowing the value at a given position to be continuous between 0 and 1 as a function of the percentage presence of the first base at a particular position,
    B) constructing a second indicator function for the test nucleic acid sequence, said second indicator function corresponding to the first base,
    C) computing the Fourier transform of each of the indicator functions,
    D) complex conjugating the Fourier transform of the second indicator function,
    E) multiplying the Fourier transform of the first indicator function and the complex conjugated Fourier transform of the second indicator function to obtain a Fourier transform indicative of a number of matches of the first base,
    F) repeating steps A–E above for a second base, a third base, and a fourth base to obtain Fourier transforms indicative of numbers of matches of each of the second, third and fourth bases,
    G) summing the Fourier transforms of the number of matches for each base, respectively, to obtain a total Fourier transform,
    H) computing the inverse Fourier transform of the total Fourier transform to obtain a complex series, and
    I) using the real part of the series to determine the total number of base matches for lags of the profile relative to the test sequence.

2. The method according to claim 1, wherein said nucleic acid sequence profile is a DNA profile.

3. The method according to claim 2, wherein said method further comprises the step of
    reverse-translating a protein profile for a set of protein sequences to obtain said DNA profile, said reverse translation being performed using codon-usage tables, said reverse translation step occurring before step (A).

4. The method according to claim 3, wherein said protein sequences are selected from the group of protein sequences consisting of transmembrane regions defined by stretches of hydrophobic residues, antigenic regions defined by stretches of hydrophilic regions, EF-hand which occurs in calcium binding proteins, helix-turn-helix motif which occurs in the DNA binding motif, zinc finger which occurs in the DNA binding motif, and glycosylation motif, a post translational protein modification.

5. The method according to claim 3, wherein said protein profile is weighted by the degree of conservation at each residue position in the alignment.

6. The method according to claim 2, wherein said DNA profile is weighted by the degree of conservation at each position in the sequence.

7. The method according to claim 1, wherein said test nucleic acid sequence has a length of from approximately 10 kilobases to approximately 100 kilobases.

8. The method according to claim 3, wherein said profile consists of from approximately 5 to approximately 30 amino acids.

9. The method according to claim 2, wherein said DNA profile is selected from the group of DNA profiles consisting of promoters and enhancers.

10. A method of computing the number of matches between a test nucleic acid sequence and a profile for a set of functionally aligned protein sequences comprising the steps of
    A) reverse-translating the profile for the set of protein sequences to a DNA profile using codon-usage tables,
    B) constructing a first indicator function for the DNA profile, said indicator function corresponding to adenine, said indicator function allowing the value at a given position to be continuous between 0 and 1 as a function of the percentage presence of adenine at a particular position,
    C) constructing a second indicator function for the test nucleic acid sequence, said indicator function corresponding to adenine,
    D) computing the Fourier transform of the first and second indicator functions,
    E) complex conjugating the Fourier transform of the second indicator function,
    F) multiplying the Fourier transform of the first indicator function and the complex conjugated Fourier transform of the second indicator function to obtain a Fourier transform indicative of a number of matches of adenine,
    G) repeating steps B–F above for guanine, thymine, and cytosine to obtain Fourier transforms indicative of numbers of matches of each of the bases,
    H) summing the Fourier transforms of the number of base matches of the adenine, guanine, thymine, and cytosine bases to obtain a total Fourier transform,
    I) computing the inverse Fourier transform of the total Fourier transform to obtain a complex series, and
    J) using the real part of the series to determine the total number of base matches for the variety of possible lags of the DNA profile relative to the test sequence.

11. The method according to claim 10, wherein said method further comprises the step of
    detecting the presence of known blocks of functionally aligned protein sequences in a test nucleic acid sequence based on the total number of base matches for the variety of possible lags between the DNA profile and the test sequence, said detecting step occurring after step (J).

12. A method of computing the number of matches between a test nucleic acid sequence and a reversed sequence of a profile for a set of functionally aligned nucleic acid sequences comprising the steps of
    A) constructing a first indicator function for the profile, said indicator function corresponding to a first base, said indicator function allowing the value at a given position to be continuous between 0 and 1 as a function of the percentage presence of the first base at a particular position, B) constructing a second indicator function for the test nucleic acid sequence, said second indicator function corresponding to the first base, C) computing a Fourier transform of each of the indicator functions, D) multiplying the Fourier transform of the first indicator function and the Fourier transform of the second indicator function to obtain a Fourier transform indicative of a number of matches of the first base, E) repeating steps A–D above for a second base, a third base, and a fourth base to obtain Fourier transforms indicative of numbers of matches of each of the second, third, and fourth bases, F) summing the Fourier transforms of the number of matches for each base, respectively, to obtain a total Fourier transform, G) computing the inverse Fourier transform of the total Fourier transform to obtain a complex series, and H) using the real part of the series to determine the total number of base matches for the variety of possible lags of the reversed sequence of the profile relative to the test sequence.

13. A system for computing the number of matches between a test nucleic acid sequence and a profile for a set of functionally aligned nucleic acid sequences comprising a central processing unit for executing instructions, a memory unit comprising an operating system a first indicator construction module for constructing four first indicator functions for the profile, said indicator functions corresponding to adenine, guanine, thymine, and cytosine, said indicator functions allowing the value at a given position to be continuous between 0 and 1 as a function of the percentage presence of each of the bases at a particular position, a second indicator construction module for constructing four second indicator functions for the test nucleic acid sequence, said second indicator functions corresponding to adenine, guanine, thymine, and cytosine, a Fourier transform module for computing the Fourier transform of each of the indicator functions, a complex conjugation module for complex conjugating the Fourier transforms of the four second indicator functions, a multiplication module for multiplying the Fourier transforms of the first indicator functions and the conjugated Fourier transforms of the second indicator functions for each of the bases, respectively, to obtain Fourier transforms for adenine, guanine, thymine, and cytosine matches, a summation module for summing the Fourier transforms of the number of matches for each base, respectively, to obtain the total Fourier transform, and a computation module for computing the inverse Fourier transform of the total Fourier transform to obtain a complex series, and for taking the real part of the series to determine the total number of base matches for the variety of possible lags of the profile relative to the test sequence, and conductive interconnects connecting the central processing unit and the memory to allow portions of the system to communicate and to allow the central processing unit to execute modules in the memory unit.

14. A method comprising:

providing a first indicator for a known nucleic acid profile, the first indicator corresponding to a first base, the first indicator including values that are related to frequencies of presence of the first base at associated positions in the profile, providing a second indicator for a test nucleic acid sequence, the second indicator corresponding to the first base, computing a Fourier transform of each of the indicators, using the Fourier transform of each of the indicators to determine a number of base matches between the profile and the test sequence.

15. The method of claim 14 wherein the first indicator is adapted to include at least three different values related to frequencies of presence of the first base for each position in the profile.

16. The method of claim 15 wherein the first indicator is adapted to include values ranging from 0 to 1, inclusive.

17. The method of claim 16 wherein the first indicator is adapted to include values ranging from 0 to 1 continuously in at least increments of 0.01.

18. The method of claim 14 wherein the using includes complex conjugating the Fourier transform of the second indicator and multiplying the Fourier transform of the first indicator and the complex conjugated Fourier transform of the second indicator to obtain a Fourier transform for the first base indicative of a number of matches of the first base in the profile and the test sequence, the method further comprising repeating the providing the first and second indicators, the computing, the complex conjugating and the multiplying for at least a second base.

19. The method of claim 18 further comprising:

summing the Fourier transforms of the number of matches for each base, respectively, to obtain a total Fourier transform;

computing an inverse Fourier transform of the total Fourier transform to obtain a complex series having a real part and an imaginary part; and using the real part of the complex series to determine a total number of base matches for possible lags of the profile relative to the test sequence;

wherein an increase in the total number of base matches indicates an increased likelihood of the presence of the profile in the test sequence.

20. The method of claim 18 wherein the values of the first indicator are dependent on frequencies of presence of each base relative to each other for each position in the profile.

* * * * *